United States Patent
Ito et al.

(10) Patent No.: US 8,351,039 B2
(45) Date of Patent: Jan. 8, 2013

(54) SPECTROSCOPY METHOD AND SPECTROSCOPE

(75) Inventors: Masafumi Ito, Osaka (JP); Norihiko Nishizawa, Nagoya (JP); Masaru Hori, Nagoya (JP); Toshio Goto, Nisshin (JP); Hiroyuki Kano, Aichi (JP)

(73) Assignee: Nu Eco Engineering Co., Ltd., Nishikamo-Gun, Aichi (JP)

( * ) Notice: Subject to any disclaimer, the term of this patent is extended or adjusted under 35 U.S.C. 154(b) by 162 days.

(21) Appl. No.: 12/926,027

(22) Filed: Oct. 21, 2010

(65) Prior Publication Data
US 2011/0063609 A1    Mar. 17, 2011

Related U.S. Application Data

(62) Division of application No. 11/991,542, filed as application No. PCT/JP2006/317683 on Sep. 6, 2006, now Pat. No. 7,855,788.

(30) Foreign Application Priority Data

| Sep. 7, 2005 | (JP) | 2005-259261 |
| Sep. 29, 2005 | (JP) | 2005-284418 |
| Sep. 29, 2005 | (JP) | 2005-284583 |
| Sep. 30, 2005 | (JP) | 2005-286506 |

(51) Int. Cl.
*G01N 21/00* (2006.01)

(52) U.S. Cl. .................................................. 356/436
(58) Field of Classification Search ................ 356/436
See application file for complete search history.

(56) References Cited

U.S. PATENT DOCUMENTS

| 6,694,067 | B1 | 2/2004 | O'Keefe et al. |
| 6,842,548 | B2 | 1/2005 | Loock et al. |
| 7,012,696 | B2 | 3/2006 | Orr et al. |
| 7,391,942 | B2 | 6/2008 | Loock et al. |
| 7,483,598 | B2 | 1/2009 | Loock et al. |
| 7,855,788 | B2 * | 12/2010 | Ito et al. ............... 356/451 |
| 2003/0007715 | A1 | 1/2003 | Look et al. |
| 2005/0201661 | A1 | 9/2005 | Look et al. |
| 2007/0252995 | A1 | 11/2007 | Shaw |

FOREIGN PATENT DOCUMENTS

| JP | 01-176920 | 7/1989 |
| JP | 10-332584 | 12/1998 |
| JP | 2000-338037 | 12/2000 |
| JP | 2001-194299 | 7/2001 |
| JP | 2001-352121 | 12/2001 |
| JP | 2004-333337 | 11/2004 |

* cited by examiner

*Primary Examiner* — Roy M Punnoose
(74) *Attorney, Agent, or Firm* — McGinn IP Law Group, PLLC

(57) ABSTRACT

A spectroscopy method, includes guiding pulse laser light to an optical fiber, which mutually reacts with a sample to be measured of a light absorptance characteristic, outputting ring down pulse light obtained through light absorption of the sample, measuring an absorptance characteristic of the sample based on an attenuation characteristic of the ring down pulse light, and setting the pulse laser light as wide-spectrum laser light, setting the optical fiber as a strong dispersive optical fiber, and increasing a pulse width of the ring down pulse light to measure a wavelength absorptance characteristic based on a ring down attenuation constant of a pulse train with respect to a time sequence corresponding to a wavelength.

4 Claims, 26 Drawing Sheets

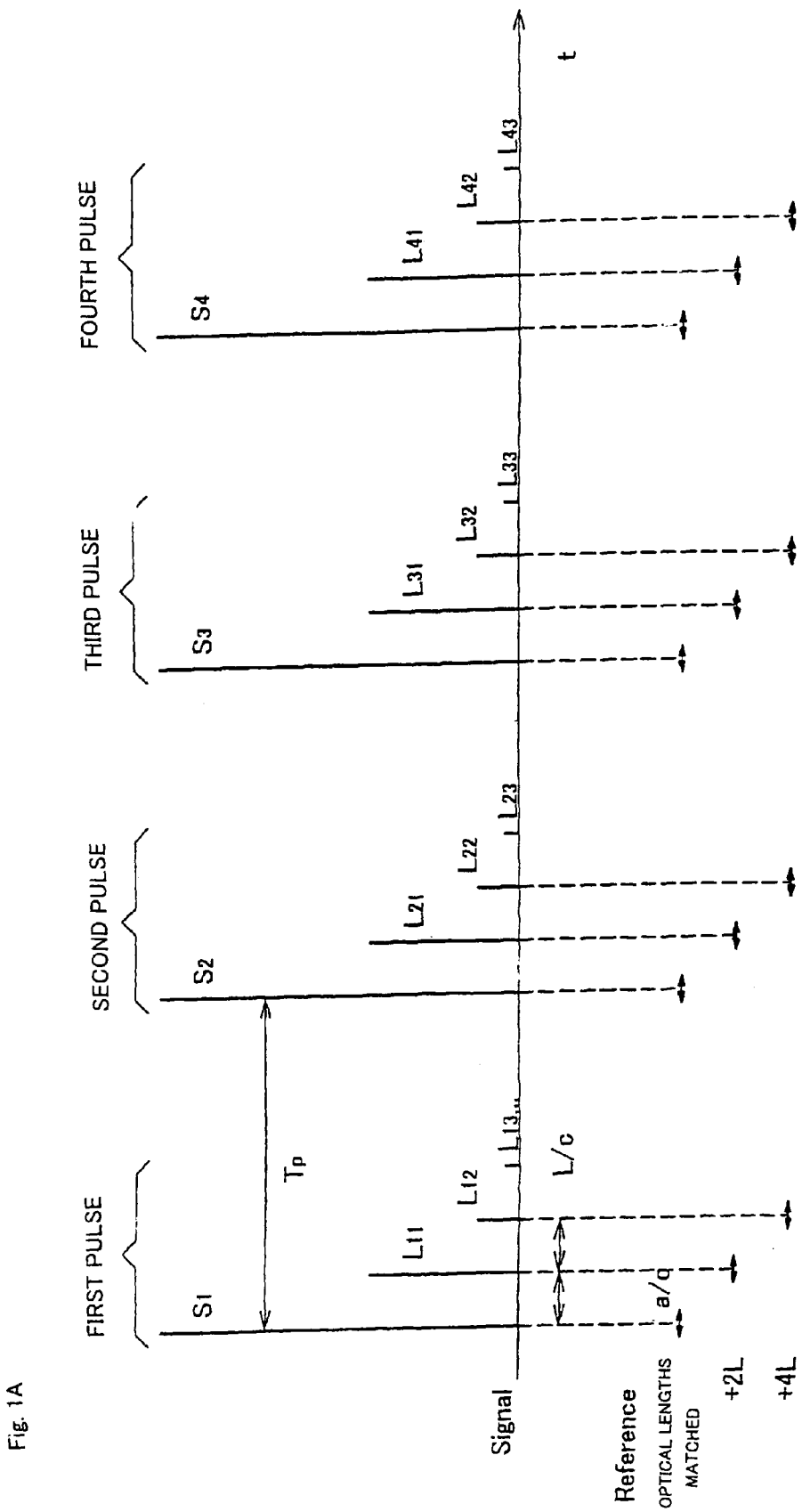

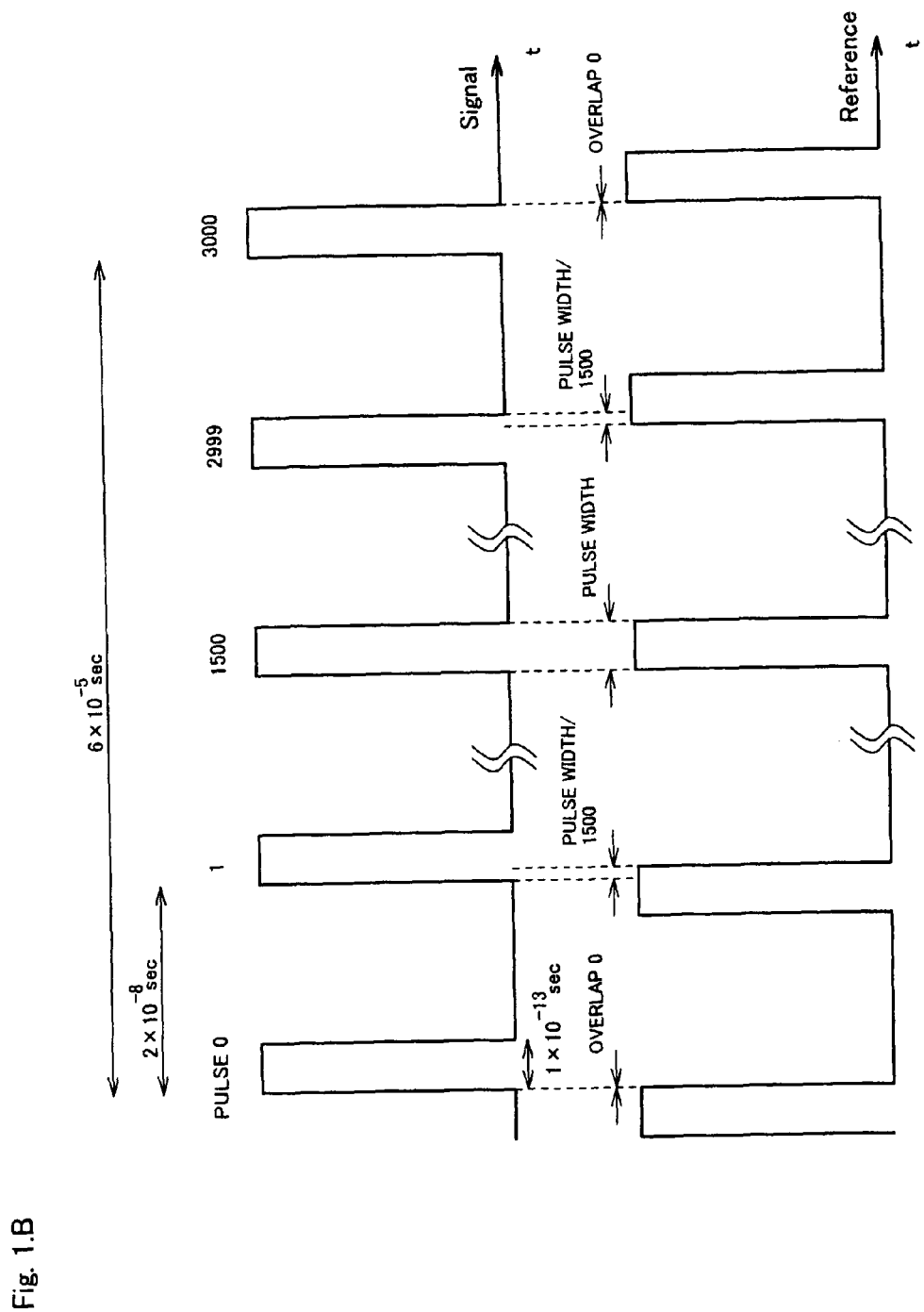
Fig. 1.B

Fig. 1.C
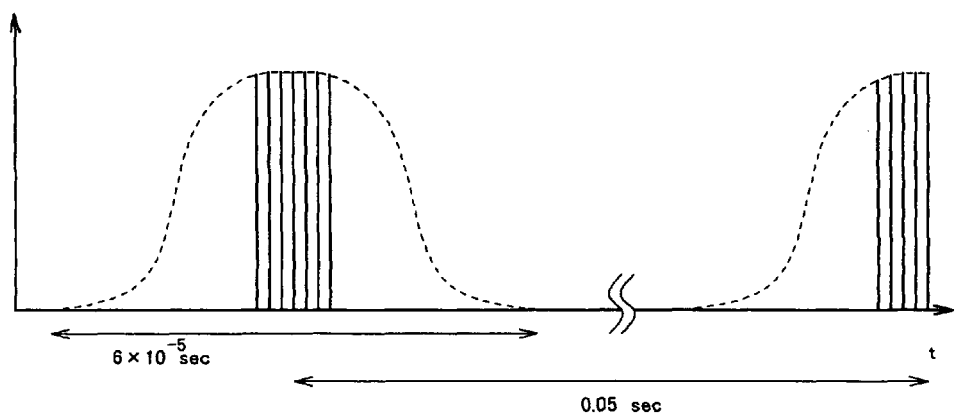
Fig. 1.D
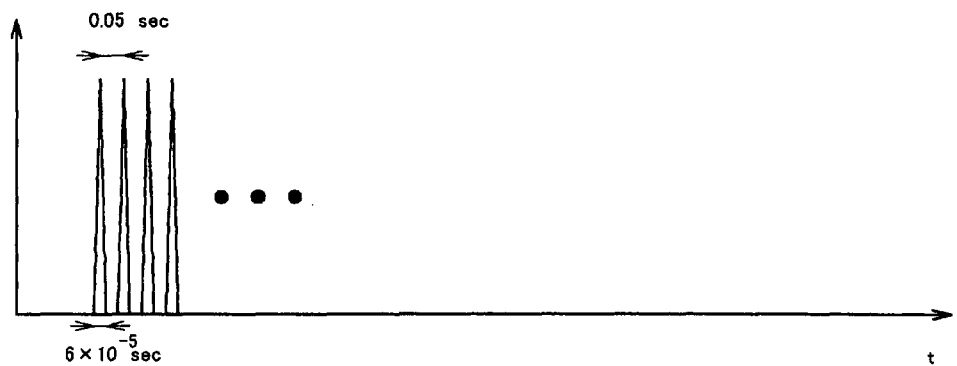
Fig. 1.E
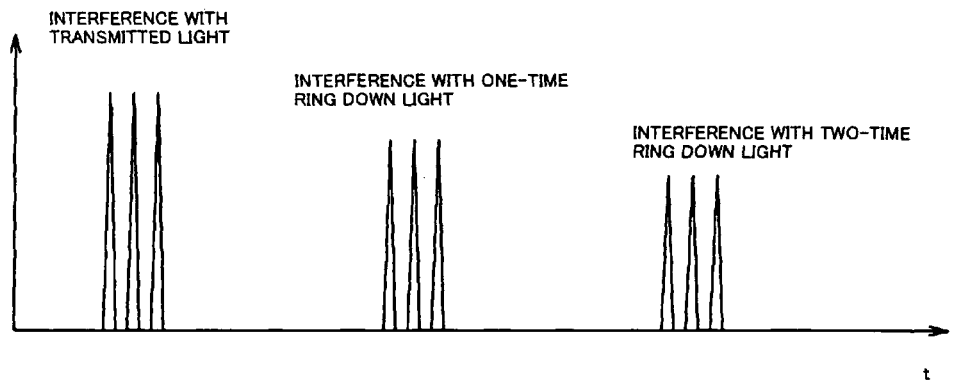

Fig. 7.A
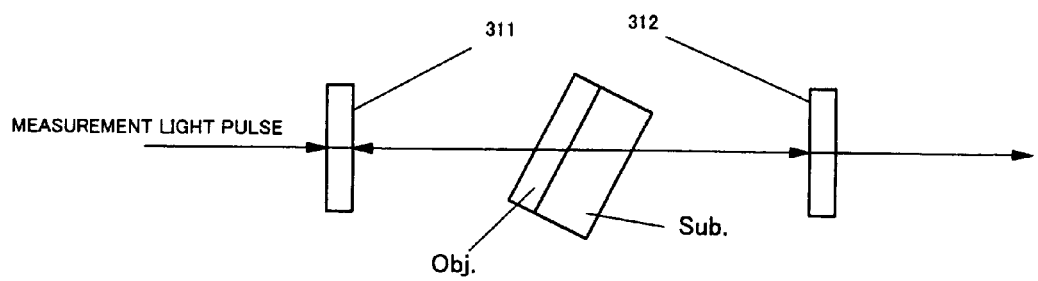
Fig. 7.B
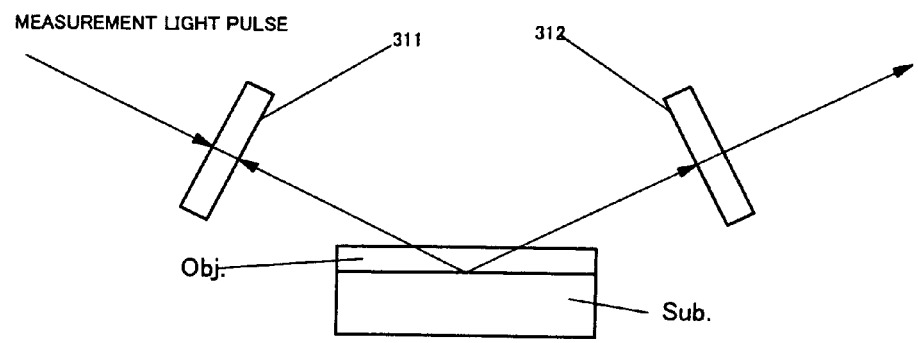
Fig. 7.C
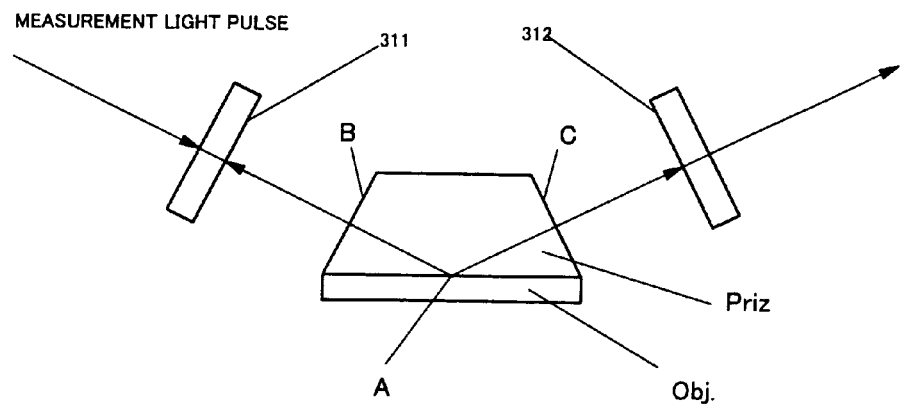

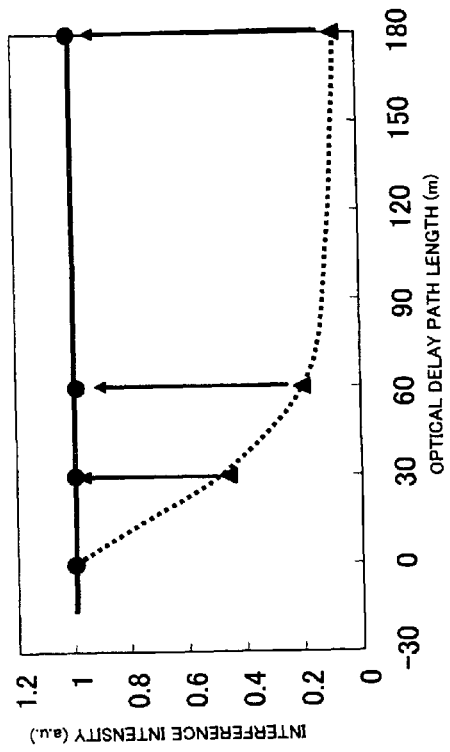
Fig. 14.A
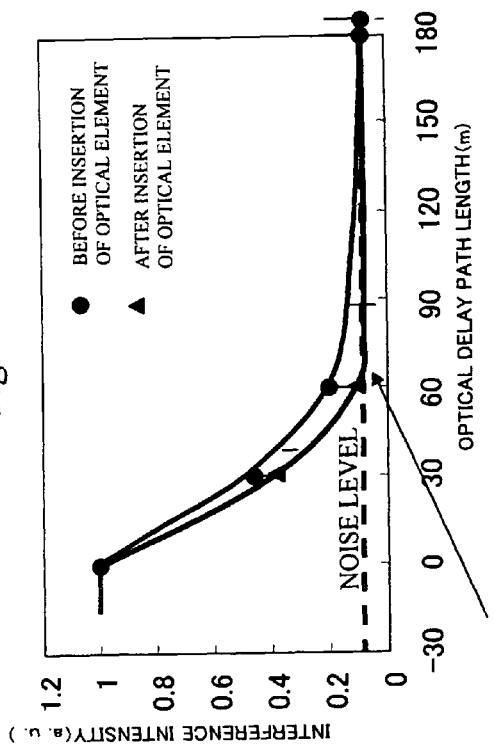
Fig. 14.B
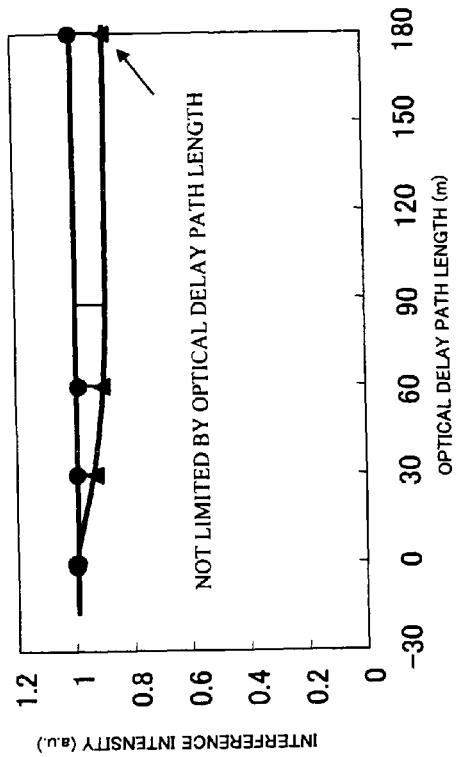
Fig. 14.C

SPECTROSCOPY METHOD AND SPECTROSCOPE

The present application is based on Japanese patent application Nos. 2005-259261, 2005-284583, 2005-284418, and 2005-286506 the entire contents of which are incorporated herein by reference.

The present Application is a Divisional application of U.S. patent application Ser. No. 11/991,542 now U.S. Pat. No. 7,855,788, filed on May 16, 2008.

DESCRIPTION

1. Technical Field

The present invention relates to a spectroscopy method and a spectroscope for analyzing chemical species adherent to a surface of a thin film formed on a substrate surface or the substrate surface with high sensitivity and measuring light absorption characteristics of a sample. In addition, the present invention relates to a spectroscopy method and a spectroscope using an optical fiber.

2. Background Art

As a method of analyzing chemical species adherent to a surface of a thin film formed on a substrate surface or the substrate surface, infrared spectroscopy has been widely used. This method is based on the fact that interatomic bonds each have a specific absorption wavelength (frequency) in an infrared region. If a sample can be filled into a cell or inserted between salt crystal plates directly or in the solution form, Fourier transform infrared spectroscopy (FTIS) is often used. In recent years, attenuated total reflection (ATR) has been employed. This method totally reflects infrared light from a transparent substrate side on a thin film formed on the transparent substrate surface to measure the degree at which the thin film absorbs evanescent waves at around an interface. The ATR has sensitivity that is about 30 times higher than permeation analysis such as FTIR.

On the other hand, cavity ring down (CRD) spectroscopy has been intensively developed in recent years. As for the cavity ring down spectroscopy, a cavity is formed using at least two mirrors, a test substance (sample) is injected into the cavity, and the sample is analyzed by spectroscopy with ring down pulse light attenuated due to light absorption of the sample in the cavity. According to the cavity ring down spectroscopy, an attenuation constant at which light intensity attenuates due to light absorption is mainly measured to thereby determine absorption coefficient of the sample for each wavelength to identify and quantitatively determine the sample. As disclosed in Patent Documents 3 and 4, known is a method of circulating pulse light in a loop fiber in place of the cavity or reciprocating pulse light in a straight fiber with the pulse light being reflected at end faces to thereby measure ring down characteristics of the pulse right.

Patent Document 1: Japanese Unexamined Patent Application Publication No. 2000-338037
Patent Document 2: Japanese Unexamined Patent Application Publication No. 2001-194299
Patent Document 3: Japanese Unexamined Patent Application Publication No. 2004-333337
Patent Document 4: U.S. Pat. No. 6,842,548B2
Patent Document 5: U.S. Pat. No. 7,012,696B2

DISCLOSURE OF INVENTION

Problems to be Solved by the Invention

However, in the case of performing the CRD spectroscopy using continuously emitted laser light, a laser in the cavity is resonated and then cut off to analyze light exiting from the cavity (ring down light).

On the other hand, a wavelength-variable soliton pulse light source for emitting light having a very small pulse width has been recently developed. Under such circumstances, the inventors of the subject application accomplish a novel CRD spectroscope using the wavelength-variable soliton pulse light source etc.

Further, a pulse light source used in conventional cavity ring down spectroscopy is inapplicable to a light source and an optical system, which use light having a pulse continuously changed in a near infrared region that is important in biospectroscopy targeted at a wavelength of 1 µm to 2 µm. A conventional light source has the following problem. That is, the light source has a pulse width on the order of ns and thus, it is difficult to reduce a cavity length to 1 cm or less from the viewpoint of avoiding interference of pulse light. For example, a 5 ns-pulse width requires the cavity length of at least 15 cm, while a 500 fs-pulse width requires the length of 150 µm. Thus, adjusting the pulse width is very effective for reduction in cavity size and observation of fast response phenomenon accompanying the size reduction but does not adapt to such wide wavelength and microcavity.

Further, a method based on optical heterodyne detection disclosed in Patent Documents 1 and 5 has been accomplished in order to increase an S/N ratio of the CRDS. However, wavelength dependency of an ultrasonic modulator, a polarizing beam splitter, or a wave plate is high, and there is no element adaptable to as wide wavelength band as 1 to 2 µm, which hinders measurement with a wide wavelength range at a high S/N ratio.

Further, any of the ring down spectroscopy methods determines absorption characteristics of a sample based on attenuation characteristics of ring down pulse light. Therefore, if the absorption characteristics of a sample involve non-linearity, a measurement value has an error, resulting in a problem of low accuracy of absorptance measurement. Further, in order to improve measurement accuracy, a ring down pulse measurement system requires a wide dynamic range with high linearity.

To give another problem, if light attenuation occurs in a measurement system, light absorptance of a sample cannot be measured unless the absorptance is higher than an attenuation coefficient of the measurement system.

In view of the above, the inventors of the present invention have examined the possibility of performing ring down spectroscopy with accuracy increased by measuring absorption characteristics of a sample under such a condition that an amplitude of light mutually reacting with the sample is fixed at a constant value and then accomplished the present invention.

Moreover, any of the above the ring down spectroscopy methods use pulse laser light. Thus, it is necessary to change a laser wavelength and execute ring down spectroscopy in order to obtain wavelength absorption characteristics of the sample.

To that end, a wavelength-variable pulse laser needs to be used as a light source.

The inventors of the present invention have examined whether the ring down spectroscopy can be executed without using a wavelength-variable pulse laser, and then completed the present invention.

The present invention has been made with a view to solving the above problems, and it is a first object of the present invention to provide novel cavity ring down spectroscopy method and spectroscope. A second object of the present invention is to enable measurement of absorption characteristics of a sample while setting an amplification factor of an optical amplifier element under such a condition that ring down light obtained by applying ring down spectroscopy to light mutually reacting with the sample does not attenuate.

It is a third object of the present invention to enable ring down spectroscopy without using a wavelength-variable pulse laser.

It is a fourth object of the present invention to improve measurement accuracy.

Means for Solving the Problems

According to one exemplary aspect of the present invention, a spectroscope for measuring a light absorption characteristic of a sample, includes: an optical fiber for guiding light to the sample to be measured of a light absorption characteristic; a first light waveguide optically coupled with the optical fiber and propagating pulse light; a processor for outputting ring down pulse light circulating or reciprocating in the optical fiber to the outside to detect and process the ring down pulse light; and a second light waveguide including a plurality light waveguides different in optical length and switchably controlling an optical length of light from a point where the light diverges from the first light waveguide to a point where the light is input to the processor, on the basis of optical length of the optical fibe.

In summary, a feature of the present invention is that plural light waveguides are switched so as to allow pulse light to reach a processing apparatus by way of a second waveguide at the same time when each ring down pulse reaches the processing apparatus.

According to another exemplary aspect of the present invention, in the spectroscope, the second light waveguide includes as many waveguides of different wavelengths as the number of ring down pulses per pulse light as a measurement target.

It is necessary to prepare as many waveguides of different wavelengths as the number of ring down pulses per pulse light as a measurement target for synchronous detection.

According to another exemplary aspect in the spectroscope, the plurality of light waveguides constituting the second light waveguide are wound around a piezoelectric tube scanner.

Since the plurality of light waveguides constituting the second light waveguide are wound around a piezoelectric tube scanner, the piezoelectric tube scanner oscillates an effective optical length to enable synchronous detection of the ring down pulse and the pulse light propagating in the second light waveguide with the processor.

According to another exemplary aspect in the spectroscope, the pulse light is a short pulse light having a pulse width of 1 ps or less. Further, ultrashort pulse light having a pulse width of 500 fs or less can be effectively used.

According to another exemplary aspect in the spectroscope, ultrashort optical pulse light is used, the light being emitted from a near infrared wavelength-variable soliton pulse light source using a femtosecond laser.

According to another exemplary aspect in the spectroscope, ultrashort optical pulse light emitted from a broadband supercontinuum light source is used.

According to another exemplary aspect, a cavity ring down spectroscopy method using signal light including a train of ultrashort optical pulses having a predetermined wavelength and a pulse width of 1 ps or less, and reference light split from the signal light, includes: successively increasing an optical length of the reference light during measurement; and performing homodyne detection of interference between the reference light and ring down light obtained by the signal light passing through a cavity. Each pulse width may be set to 500 fs or less.

According to another exemplary aspect in the cavity ring down spectroscopy method, a train of ultrashort optical pulses is used, the pulses being emitted from a near infrared wavelength-variable soliton pulse light source using a femtosecond laser. Further, according to another exemplary aspect, in the cavity ring down spectroscopy method, a train of ultrashort optical pulses emitted from a broadband supercontinuum light source is used.

According to another exemplary aspect a cavity ring down spectroscope, includes: a light source for emitting a train of ultrashort optical pulses having a predetermined wavelength and a pulse width of 1 ps or less; a light split means for diverging pulse trains output from the light source; a cavity that can set a sample in an optical path having two high-reflection mirrors connected to a first light output of the light split means and defined by the two high-reflection mirrors; a wavelength-variable optical path portion connected to a second light output of the light split means and having a variable optical length; and homodyne detecting means for outputting interference between a light output of the cavity and a light output of the variable-wavelength optical path portion as an electric signal. Each pulse width may be set to 500 fs or less.

According to another exemplary aspect in the cavity ring down spectroscope, the variable-wavelength optical path portion is provided with a movable mirror capable of oscillating and changing its position.

According to yet another exemplary aspect, a spectroscopy method, includes: propagating light to an optical fiber for guiding the light to a sample to be measured of a light absorption characteristic and measuring a light absorptance characteristic of the sample; and inserting an amplifying element for amplifying the light to the optical fiber.

According to yet another exemplary aspect in the spectroscopy method, wherein the light is stepped-down light or pulse light, and the method further includes: setting an amplification factor of the amplifying element to an amplification factor at which ring down light of the light does not attenuate before setting a sample, and setting the sample to measure ring down light; and measuring an absorptance coefficient of the sample based on an attenuation characteristic of the ring down light.

According to yet another exemplary aspect in the spectroscopy method, the light is stepped-down light or pulse light, and the method further includes: setting a sample to measure ring down light; controlling an amplification factor of the amplifying element not to attenuate the ring down light; and measuring an absorptance coefficient of the sample based on the amplification factor.

In the above three methods, the optical fiber may have a loop shape so as to circulate light in the loop optical fiber or have a linear shape with both ends used as reflection surfaces to reciprocate light.

The light may be laser or an LED light source. Examples of the laser include a general semiconductor laser and other solid lasers or gas lasers. If a wavelength-variable laser is used, a wavelength absorption characteristic of a sample can be measured. If a broadband supercontinuum light laser is used, a wavelength of ring down light received with the light receiving element is analyzed to determine wavelength absorption characteristics.

The light may be continuous light, stepped-down light, or pulse light. The stepped-down light may be obtained by cutting the light output from a light source or outputting pulses. Another conceivable method is to reduce optical coupling with an optical fiber with respect to light output from a light source or increase coupling in a pulsed manner. Reducing optical coupling with the optical fiber stepwise means stepwise reduction in amplitude of light introduced to the optical fiber.

Pulsed optical coupling means short-term optical coupling. Therefore, an amplitude of light incident on the optical fiber corresponds to a step-down function or a pulse function. Further, if a polarizing direction of light output from the light source is controlled, the light propagating in the optical fiber corresponds to the step-down function or the pulse function. The stepwise change means sudden change in polarizing direction from one to another. The pulsed change means suddenly changing the polarizing direction to one direction and chanting the direction to the original polarizing direction or another polarizing direction.

A feature of the present invention resides in insertion of an amplifying element for amplifying light to an optical fiber, which mutually reacts with a sample. According to yet another exemplary aspect, in the spectroscopy method, the light is stepped-down light or pulse light, and the method further includes: setting an amplification factor of the amplifying element to an amplification factor at which ring down light of the light does not attenuate before setting a sample, and setting the sample to measure ring down light; and measuring an absorptance coefficient of the sample based on an attenuation characteristic of the ring down light. According to yet another exemplary aspect, in the spectroscopy method the light is stepped-down light or pulse light, and the method further includes: setting a sample to measure ring down light; controlling an amplification factor of the amplifying element not to attenuate the ring down light; and measuring an absorptance coefficient of the sample based on the amplification factor.

According to still another exemplary aspect, a spectroscope for measuring a light absorption characteristic of a sample, includes: an optical fiber that allows light to react with the sample to be measured of a light absorption characteristic; an amplifying element for amplifying the light; a detection element for detecting indentify of the light propagating in the optical fiber; and a processor for controlling an amplification factor of the amplifying element in accordance with intensity of the light detected with the detection element to determine an absorption characteristic of the sample.

A feature of the present invention resides in insertion of an amplifying element for amplifying light to an optical fiber, which mutually reacts with a sample to thereby set an amplification factor of the amplifying element in accordance with intensity of light propagating in the optical fiber to measure an absorptance characteristic of the sample.

According to still another exemplary aspect, in the spectroscope, the light is stepped-down light or pulse light, and the processor sets an amplification factor of the amplifying element to an amplification factor at which ring down light of the light does not attenuate before setting a sample, and sets the sample to measure ring down light to measure an absorptance coefficient of the sample based on an attenuation characteristic of the ring down light.

According to still another exemplary aspect, in the spectroscope, the light is stepped-down light or pulse light, and the processor sets a sample to measure ring down light, controls an amplification factor of the amplifying element not to attenuate the ring down light, and measures an absorptance coefficient of the sample based on the amplification factor.

According to still another exemplary aspect, in the spectroscope, the light is continuous light or pulse light, and the processor controls an amplification factor of the amplifying element to a predetermined value and measures an absorption characteristic of the sample based on the amplification factor or an attenuation amount.

Even if the light is continuous light, an adsorption characteristic of the sample can be determined. An amplitude of light circulating or reciprocating in the optical fiber converges to a value at which an incident amount of light to the optical fiber, a loss due to absorptance of the sample, and a loss in another optical fiber system are balanced. If no sample is set, no absorption occurs, so an amplitude of light propagating in the optical fiber is increases as compared with the case the sample is set. Thus, if an amplification factor is controlled to set an amplitude of light propagating in the optical fiber to a predetermined value based on the difference, an adsorption characteristic of the sample can be measured based on the amplification factor.

Likewise, if no sample is set, an amplification amount can set such that a loss of an optical fiber system is 0 to measure an absorption characteristic based on an attenuation amount measured when a sample is set.

According to still another exemplary aspect, a spectroscopy method, includes: guiding pulse laser light to an optical fiber, which mutually reacts with a sample to be measured of a light absorptance characteristic; outputting ring down pulse light obtained through light absorption of the sample; measuring an absorptance characteristic of the sample based on an attenuation characteristic of the ring down pulse light; and setting the pulse laser light as wide-spectrum laser light, setting the optical fiber as a strong dispersive optical fiber, and increasing a pulse width of the ring down pulse light to measure a wavelength absorptance characteristic based on a ring down attenuation constant of a pulse train with respect to a time sequence corresponding to a wavelength.

The optical fiber may have a loop shape so as to circulate light in the loop optical fiber or have a linear shape with both ends used as reflection surfaces to reciprocate light.

The light may be laser or an LED light source. Examples of the laser include a general semiconductor laser and other solid lasers or gas lasers. If wide-spectrum laser light is used, and a strong dispersive optical fiber is used, a phase velocity for each wavelength. The present invention is accomplished utilizing this phenomenon. The broadband supercontinuum laser light is obtained as follows. If laser light having a ultrashort pulse width (for example, soliton wave laser light) is incident to a nonlinear dispersion shift fiber having a length of about 5 mm, broadband supercontinuum laser light having a continuous spectrum in a range of 1.25 µm to 1.95 µm is obtained. If a 200 m-long nonlinear dispersion shift fiber is used, broadband supercontinuum laser light having a continuous spectrum in a range of 1.0 µm to 2.2 µm is obtained (Norihiko Nishizawa, Toshio Goto, "Solid Physics" Vol. 39, No. 10, (2004), pp. 665-678).

According to another exemplary aspect, a spectroscope for measuring a light absorption characteristic of a sample, includes: an optical fiber for guiding laser pulse light to the sample to be measured of a light absorption characteristic; a laser device for generating wide-spectrum laser pulse light; and a processor for increasing a pulse width of ring down pulse light circulating or reciprocating in the optical fiber, outputting the ring down pulse light to the outside, and measuring a wavelength absorptance characteristic based on a ring down attenuation constant of a pulse train with respect to a time sequence corresponding to a wavelength in accordance with an attenuation characteristic of the ring down pulse light.

As the laser light, broadband supercontinuum laser light is preferably used, for example, as above.

According to another exemplary aspect, the spectroscope, further includes: a first light waveguide optically coupled with the optical fiber; and an optical directional coupling element for optically coupling the first light waveguide with the optical fiber; the first light waveguide having one end connected to the laser device and the other end connected to a light receiving element of the processor, which receives the ring down pulse light.

According to another exemplary aspect, in the spectroscope, wherein another optical coupling element provided separately from the optical directional coupling element in the optical fiber is used to output the ring down pulse light to a second light waveguide different from the first light waveguide, and the second light waveguide is connected to the light receiving element of the processor.

A feature of the present invention is that a laser light input system and a ring down pulse light input system are separately provided.

Advantages of the Invention

According to the exemplary aspect, pulse light propagating through the first light waveguide partially splits and enters the optical fiber. In the optical fiber, pulse light is attenuated to ring down pulse light due to light adsorption of the sample. The resultant ring down pulse lights are output from the optical fiber and incident on the processor. On the other hand, pulse light propagating in the first light waveguide splits and then enters the processor through one light waveguide selected from waveguides of the second light waveguide. At this time, a given ring down pulse light and the original pulse light reach the processor at the same time. Hence, synchronous detection of the ring down pulse light can be performed. If light waveguides constituting the second light waveguide are changed, the ring down pulse light that travels a distance corresponding to the optical length of the light waveguide and the original pulse light reach the processor at the same time, which enables synchronous detection of the ring down pulse light.

According to the another exemplary aspect, each waveguide of the second light waveguide is selected in sync with the pulse light to thereby enable synchronous detection of a desired number of ring down pulse lights.

According to claim 3, the light waveguides constituting the second light waveguide are made up of an optical fiber wound around a piezoelectric tube scanner. Thus, the piezoelectric tube scanner is enlarged/reduced to extend or reduce the optical fiber to electrically change an optical length. The piezoelectric tube scanner is electrically changed in size to oscillate an optical path about some position of the path with a certain amplitude. Then, an optical length that allows the ring down pulse light and the original pulse light to reach the processor at the same time is within the amplitude of oscillation.

According to the another exemplary aspect, if the pulse light is a short pulse light having a pulse width of 1 ps or less, high-sensitivity cavity ring down spectroscopy can be performed based on synchronous detection even if an optical fiber length is short. Ultrashort pulse light having a pulse width of 500 fs or less is more desirable. Further, since a pulse width for synchronous detection is narrow, measurement accuracy is increased and the apparatus can be downsized. Such an optical system is effective for analysis of a small amount of sample, for example, quantitative determination of a thin film or identification of chemical species adherent to the surface.

According to the another exemplary aspect, a wavelength is analyzed to measure wavelength adsorption characteristics of the sample.

If the ultrashort pulse light having a pulse width of 1 ps or less is used, high-sensitivity cavity ring down spectroscopy can be performed based on homodyne detection. Such an optical system is effective for analysis of a small amount of sample, for example, quantitative determination of a thin film or identification of chemical species adherent to the surface. The pulse width may be 500 fs or less.

A pulse train is split to two optical paths, one of which is guided to the cavity and the other of which is guided to an optical path provided with a movable mirror that can change an optical length. The interference between the optical pulse train in the optical path with a variable length and the pulse train of the ring down light passed through the cavity is measured. If the optical length on the movable side is increased such that an optical path of a pulse matches with that of the ring down light, intensity of ring down light can be detected in order from plural pulses. The movable mirror is set oscillating and then moved to thereby set timings at which "the optical length matches with that of the ring down light". As a result, initial adjustment is facilitated and each ring down light can be securely measured through homodyne detection.

In the method according to the yet another exemplary aspect, and the Spectroscope, an amplifying element for amplifying the light is inserted to the optical fiber. Thus, an absorption coefficient of the sample can be measured while a loss in measurement system or sample is compensated for. Therefore, high-accuracy measurement can be performed.

Further, in the method according to yet another exemplary aspect, and the spectroscope according to the yet another exemplary aspect, the light is stepped-down light or pulse light. Thus, attenuation characteristics of ring down light of this light can be used for measurement. An amplification factor of the amplifying element is set to an amplification factor at which ring down light of the light does not attenuate to thereby compensate for a loss in measurement system to measure an absorptance of the sample. Thus, measurement accuracy of the absorptance of the sample is improved. That is, according to the present invention, attenuation characteristics of the ring down light due to absorption of the sample are measured, and the absorption characteristics of the sample are measured.

Further, in the method according to yet another exemplary aspect and the spectroscope according to still another exemplary aspect, a sample is set to measure ring down light, an amplification factor of the amplifying element is controlled not to attenuate the ring down light, and an absorptance coefficient of the sample is measured based on the amplification factor.

That is, the light absorption of the sample causes ring down light, but the amplification factor of the amplifying element is subjected to feedback control not to cause the ring down to measure absorption characteristics of the sample at any intensity. That is, nonlinear characteristics of the absorption characteristics can be measured. Since an amplitude of light is set constant, measurements involve few error and measurement accuracy is improved.

Further, according to still another exemplary aspect, the light is continuous light, and the processor controls an amplification factor of the amplifying element to a predetermined value and measures an absorption characteristic of the sample based on the amplification factor or an attenuation amount. In this case as well, it is possible to perform measurement of absorptance of the sample while compensating for a loss in measurement system or setting light intensity constant.

Further, in the method according to another exemplary aspect, and the spectroscope according to the another exemplary aspect, wide-spectrum laser light is used, and a strong dispersive optical fiber is used. The strong dispersive optical fiber changes its phase velocity for each wavelength. Thus, a ring down pulse light period varies for each wavelength. Therefore, the ring down pulse light propagates a longer distance of optical fiber as the number of ring down operations increases. Thus, a time width of pulse laser light is increased. A ring down attenuation coefficient of a pulse train corresponding to a time sequence corresponding to each wavelength is measured based on the attenuation characteristic of the ring down pulse light train to determine attenuation coefficients with each wavelength. As a result, wavelength absorption characteristics can be obtained at a time to enable identification of the sample.

According to the spectroscope according to another exemplary aspect, one optical directional coupling element is used to enable input and output of pulse laser light to/from the optical fiber. Thus, the apparatus structure is simplified.

According to the spectroscope according to still another exemplary aspect, different directional coupling elements are used to input and output pulse laser light to/from the optical fiber. Thus, pulse laser light output from the laser device never enters the light receiving element, so high-accuracy detection of the ring down pulse is achieved.

BRIEF DESCRIPTION OF DRAWINGS

FIG. 1A is a first graph illustrating how to perform synchronous detection according to an embodiment of the present invention;

FIG. 1B is a second graph illustrating how to perform synchronous detection according to the embodiment of the present invention;

FIG. 1C is a third graph illustrating how to perform synchronous detection according to the embodiment of the present invention;

FIG. 1D is a fourth graph illustrating how to perform synchronous detection according to the embodiment of the present invention;

FIG. 1E is a fifth graph illustrating how to perform synchronous detection according to the embodiment of the present invention;

FIG. 7 is a diagram showing three methods for setting a substrate having a sample attached thereonto in a cavity region;

FIG. 14A is a characteristic chart illustrating why a long light delay optical path cannot be used if the semiconductor optical amplifier is not used in the apparatus of Example 5;

FIG. 14B is a characteristic chart showing how interference intensity relative to the light delay optical path length is improved by inserting a semiconductor optical amplifier in the apparatus of Example 5;

FIG. 14C is an explanatory view showing how a semiconductor optical amplifier is inserted in the apparatus of Example 5 to elongate a light delay optical path that is applicable to increase measurement accuracy of an absorption factor;

DESCRIPTION OF REFERENCE NUMERALS

Figure 2:
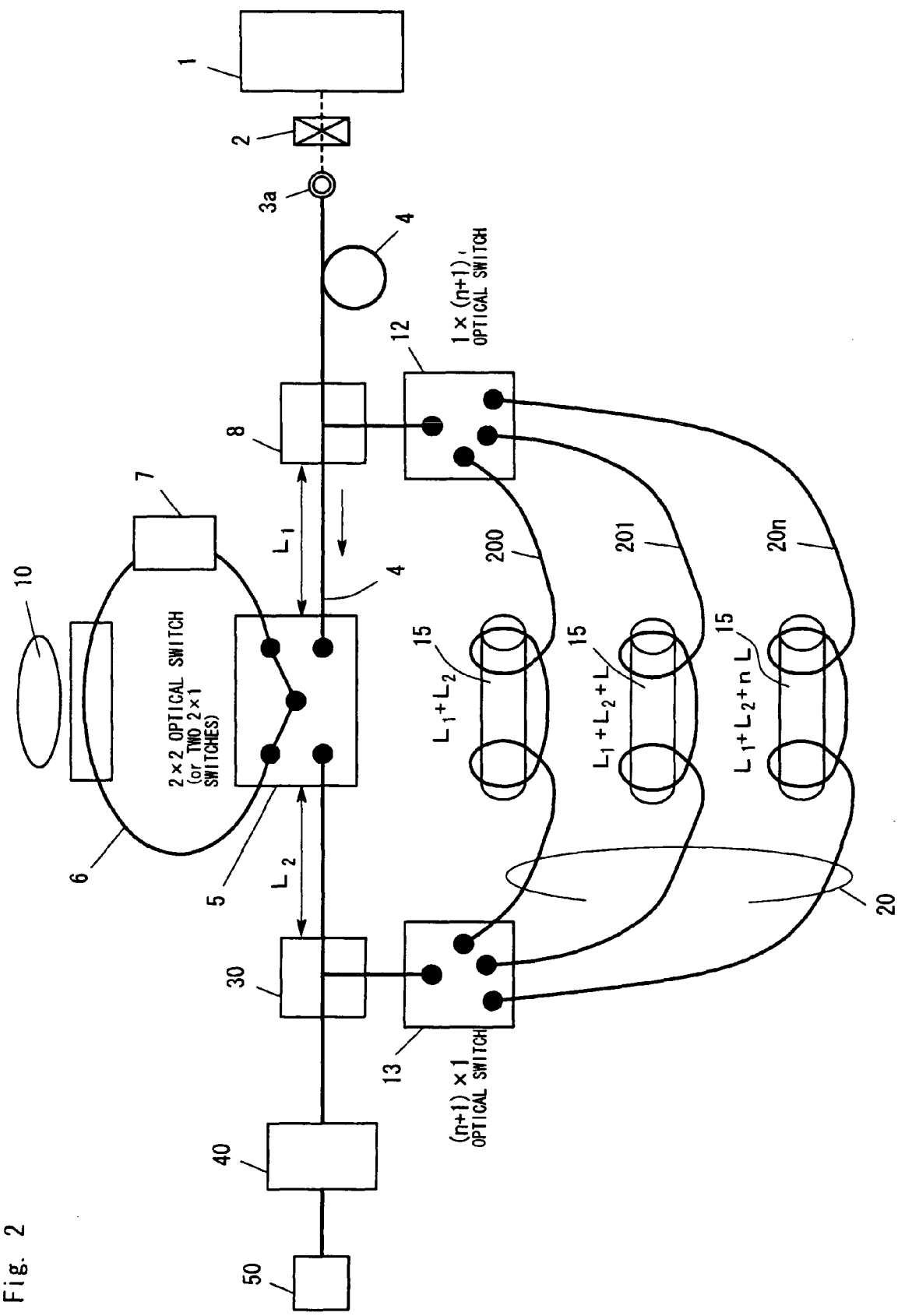
FIG. 2 is a block diagram specifically showing the structure of a ring down spectroscope according to Example 1 of the present invention.

1: wavelength-variable femtosecond soliton pulse light source
2: ½-wavelength plate
3a: sphere lens
4: first light waveguide
5: wavelength selective switch
6: optical fiber
7: optical amplifier
8: optical directional coupler
12: first optical switching element
13: second optical switching element
15: piezoelectric tube scanner
20: second light waveguide
200, 201, . . . , 20n, . . . : light waveguides of second light waveguide
30: fiber coupler
40: homodyne detector
50: processor 301: wavelength-variable femtosecond soliton pulse light source
302: $\lambda;2$-wavelength plate
303a, 303b: sphere lens
304: polarization maintaining fiber
305: beam splitter
306: polarizing beam splitter
307: $\lambda;4$-wavelength plate
308: galvano mirror
311, 312: high-reflective mirror
321, 322: biconvex lens
330: fiber coupler
331, 332, 331', 332': optical fiber
340: balanced detector
350: A/D converter and digital processing device
410, 490: optical fiber
421: second polarizer
422: first polarizer
423: faraday rotator
412: first light waveguide
413: second light waveguide
415: optical amplifying element
436, 437: optical directional coupling element
510, 590: optical fiber
521: second polarizer
522: first polarizer
523: faraday rotator
512: first light waveguide
513: second light waveguide
536, 537: optical directional coupling element

BEST MODES FOR CARRYING OUT THE INVENTION

Hereinafter, embodiments of the present invention will be described with reference to the drawings. The present invention is not limited to the following embodiments. To begin with, synchronous detection of the embodiments is described.
First Embodiment First, pulse light circulates in a loop-type optical fiber. The optical fiber and a sample react with each other, and pulse light is successively attenuated into ring down pulse light (pulse train) due to light absorption of a sample. The resultant ring down pulse lights are input to an external processing apparatus. Provided that L represents an optical length of a loop optical fiber, a difference in optical length between ring down pulse lights is L. If c represents light velocity, a time interval between adjacent ring down pulse rights is L/c. That is, as shown in FIG. 1A, some of pulse lights, transmitted lights $S_1$, $S_2$, $S_2$, $S_4$, . . . , are incident to the processing apparatus without circulating in the optical fiber. Further, one-time ring down pulse light $L_{11}$ that takes a round in the loop optical fiber is output and input to the processing apparatus with a delay of L/c from the arrival of the transmitted light $S_1$. Then, two-time ring down pulse light $L_{12}$ that takes two rounds in the loop optical fiber is output and input to the processing apparatus with a delay of L/c from the arrival of the ring down pulse light $L_{11}$. In this way, ring down pulse lights are successively output from the optical fiber and input to the processing apparatus at intervals of L/c. This operation applies to the transmitted lights $S_2$, $S_2$, and $S_4$ and ring down pulse lights thereof. If the optical length L of the optical fiber and a pulse interval $T_P$ are adjusted, a pair of ring down pulse lights following one transmitted light can be prevented from overlapping the next transmitted light with ease. Hereinafter, the transmitted light (pulse light not absorbed to the sample) and the ring down pulse lights are referred to as signal light.

On the other hand, pulse light propagates through a second light waveguide as a path different from the loop optical fiber and then enters the processing apparatus. The pulse light is referred to as reference light (reference). The ring down pulse lights including the transmitted light are detected in sync with the reference light. Specific examples of available detection methods include homodyne detection and differential detection that are based on a correlation between signal light and reference light. If an optical length of a propagation path of reference light is completely equal to an optical length of a propagation path of transmitted light, the detection of the transmitted light in sync with the reference light produces a pulse having an amplitude that is the product of an amplitude of the transmitted light and an amplitude of the reference light. This detection output is represented by A. Next, if an optical length of a propagation path of reference light is completely equal to an optical length of a propagation path of one-time ring down light, the detection of the transmitted light in sync with the reference light produces a pulse having an amplitude that is the product of an amplitude of the transmitted light and an amplitude of the reference light, that is, an amplitude obtain by modulating an amplitude of reference light with an amplitude of signal light. This detection output is represented by $\alpha A (0<\alpha<1)$. Likewise, if an optical length of reference light is completely equal to an optical length of n-time ring down pulse light, the detection output of $\alpha^n A$ $(0<\alpha<1)$ is obtained.

However, it is difficult to completely match an optical length of a propagation path of reference light with an optical length of a propagation path of transmitted light and each ring down pulse light. This is because signal light having a short pulse width is used. To that end, provided in the propagation path of reference light is a light waveguide such as an optical fiber wound around a piezoelectric tube scanner having an optical length that is vibrationally changeable with respect to a reference optical length. As a result, adjacent pulses of reference light travel different optical lengths due to oscillations of the piezoelectric tube scanner. A pulse interval of the reference light becomes longer than a pulse interval of the reference optical length in the direction in which an optical length increases. In contrast, the pulse interval becomes shorter in the direction in which an optical length decreases. At this time, if an oscillation amplitude a of the optical length is shorter than the optical length L of the optical fiber, a change a/c in incident time, that is, the time when the pulse light is input to the processing apparatus, due to change in pulse interval of the reference light can be smaller than the time interval L/c between the adjacent ring down pulse lights. In this way, an optical length of a propagation path of reference light split from signal light having a given pulse frequency (pulse interval) is adjusted by oscillation with respect to the reference optical length to thereby achieve the reference light having an optical length almost equal to the optical length of transmitted light and each ring down pulse light.

Referring to FIG. 1B etc., synchronous detection of two pulse trains of this embodiment is described based on concrete numeric values. The signal light is pulse light having a pulse width of 100 fs ($1\times10^{-13}$ seconds) and a pulse interval of $2\times10^{-8}$ seconds (pulse frequency of 50 MHz). The oscillation frequency of the piezoelectric tube scanner of the second light waveguide through which reference light propagates is set to 80 Hz. The optical length of the signal light is equal to the optical length of reference light that is adjusted based on the reference optical length of the second light waveguide. An oscillation amplitude of the second light waveguide is changed by ±2 mm in terms of optical length.

A time function of an optical length x is expressed as follows: $x=2 \sin 160\pi t + x_0$. In this expression, $x_0$ represents a reference optical length. A change rate v (mm/sec) of the optical length is expressed as follows: $v=320 \sin 160\pi t$. As for a speed at around the center of simple harmonic oscillation, $v=1000$ mm/sec when $t=0$. Then, the optical length is changed by $2\times10^{-8}$ m only, during a period corresponding to a reference light pulse interval of $2\times10^{-8}$ seconds. This means that a pulse interval of reference light propagating through the second light waveguide increases or decreases by $6.67\times10^{-17}$ seconds.

Then, if a 0th pulse of the signal light and that of the reference light passed through the second light waveguide are input to the processing apparatus with a difference corresponding to a pulse width of $1\times10^{-13}$ seconds, and the pulse of the reference light is input ahead of that of the signal light with a pulse interval longer than that of the signal light by $6.67\times10^{-17}$ seconds as shown in FIG. 1B, for example, $1\times10^{-13}$ sec/$6.67\times10^{-17}$ sec=1500, so a pulse of signal light matches a pulse of reference light at a 1500th pulse. A delay corresponding to a pulse width of $1\times10^{-13}$ seconds occurs between the signal light and the reference light at a 3000th pulse. At this time, the pulse of the reference light is input later than that of the signal light. A pulse interval of the signal light is $2\times10^{-8}$ seconds, so a time interval between the 0th pulse and the 3000th pulse is $6\times10^{-5}$ seconds. During this period, the optical length is changed by 60 μm.

In the case of brining about interference between the signal light and the reference light and performing synchronous detection thereof, the detection output of FIG. 1C is obtained. The signal light interferes with the reference light during the 3000 pulses under the condition of FIG. 1B. The detection output is just 0 at the 0th pulse, maximum at the 1500th pulse, and just 0 at the 3000th pulse. During this period, 2999 peaks appear under the envelop (as indicated by the dotted line) of FIG. 1C. The envelop and 2999 peaks under the envelop appear for $6\times10^{-5}$ seconds and then disappear till 0.025 seconds later; after the elapse of the 0.025 seconds, the optical length of the second light waveguide is returned to the original length. That is, the envelop and 3000 peaks within the envelope appear for $6\times10^{-5}$ seconds at intervals of 0.025 seconds. Otherwise these disappear.

Considering this phenomenon from a microscopic angle, very sharp peaks appear with a width of $6\times10^{-5}$ seconds at intervals of 0.0125 seconds (see FIG. 1D). The same applies to other pulse waveforms, not a rectangular waveform of FIG. 1B and to a wide range around the center of simple harmonic oscillation.

As for a difference in interference degree between the 1500th pulse and pulses adjacent to the 1500th pulse as shown in FIG. 1B, one pulse includes 18.4 wave lengths and the phase difference is as small as $2\pi/80$ at the wavelength of 1.63 μm, for example. In this case, an intensity of interference in plural pairs of signal light and reference light at around any peak of the envelope is substantially equal to that at the peak of the envelope. Thus, it is unnecessary to completely match phases of the signal light pulse and the reference light pulse. Further, it is unnecessary to exactly match a reference optical length of each light waveguide of the second light waveguide with an optical length of each ring down pulse light. An allowable error therebetween is about an amplitude of oscillation of the optical length (in the above example, ±2 mm) or less. That is, it is only necessary to match the optical length of the ring down pulse light and that of the reference light within a range in which the optical length varies.

Therefore, a reference optical length of the 0th light waveguide of the second light waveguide only has to match each of the optical lengths of the transmitted lights $S_1$, $S_2$, $S_2$, $S_4$, . . . of FIG. 1A within the error corresponding to an amplitude of oscillation of the optical length. Likewise, a reference optical length of the wavelength-variable femtosecond soliton pulse light source 1st light waveguide of the second light waveguide only has to match each of the optical lengths of the one-time ring down pulse lights $L_{11}$, $L_{21}$, $L_{31}$, $L_{41}$, . . . of FIG. 1A within the error corresponding to an amplitude of oscillation of the optical length. Likewise, a reference optical length of the ½-wavelength plate 2nd light waveguide of the third light waveguide only has to match each of the optical lengths of the two-time ring down pulse lights $L_{12}$, $L_{22}$, $L_{32}$, $L_{42}$, . . . of FIG. 1A within the error corresponding to an amplitude of oscillation of the optical length. Likewise, Likewise, a reference optical length of the nth light waveguide of the nth light waveguide only has to match each of the optical lengths of the n-time ring down pulse lights $L_{1n}$, $L_{2n}$, $L_{3n}$, $L_{4n}$, . . . of FIG. 1A within the error corresponding to an amplitude of oscillation of the optical length. In this way, if the optical length of each light waveguide of the second light waveguide is set, as shown in FIG. 1E, synchronous detection of the transmitted light and reference light propagated through the 0th light waveguide, synchronous detection of the one-time ring down pulse light and reference light propagated through the wavelength-variable femtosecond soliton pulse light source 1st light waveguide, results of synchronous detection of the two-time ring down pulse light and reference light propagated through the ½-wavelength plate 2nd light waveguide, and synchronous detection of the n-time ring down pulse light and reference light propagated through the nth light waveguide give plural very-sharp pulse groups with a width of $6\times10^{-5}$ seconds.

EXAMPLE 1

FIG. 2 is a block diagram showing the structure of a ring down spectroscope 100 using a loop optical fiber having a length of about 150 m according to Example 1 of the present invention. The ring down spectroscope 100 includes a first light waveguide 4 including a wavelength-variable femtosecond soliton pulse light source 1, a ½-wavelength plate 2, a sphere lens 3a, and an optical fiber. The first light waveguide 4 is coupled with a loop optical fiber 6 through a wavelength selective switch 5. The loop optical fiber 6 is coupled with a sample 10 mutually reacting with pulse light propagating through the optical fiber. The optical fiber 6 is provided with an optical amplifier 7 for appropriately adjusting a factor of attenuation of ring down pulse light due to light absorption of the sample 10. The optical amplifier 7 may be omitted. However, if the optical amplifier 7 appropriately amplifies the ring down pulse light, light absorption characteristics of the sample can be measured with high accuracy and sensitivity. The first light waveguide 4 is connected to a homodyne detector 40 through a fiber coupler 30. A synchronous detection signal (see FIG. 1E) output from the homodyne detector 40 is A/D converted with a digital processor 50 to determine an attenuation coefficient of the ring down pulse light to measure absorption characteristics of the sample.

On the other hand, an optical directional coupler 8 is provided to the first light waveguide 4, and a first optical switching element 12 is connected to its node. The first optical switching element 12 selectively branches pulse light diverging from the first light waveguide 4 to (n+1) light waveguides difference in reference optical length. Here, provided are light waveguides 200, 201, 202, . . . , and 20n, which are made up of an optical fiber wound around each of (n+1) piezoelectric tube scanners 15. These waveguides effectively change their optical lengths due to piezoelectric effects of an electric signal. To elaborate, an amplitude of oscillation is set to 2 mm. The (n+1) light waveguides constitute a second light waveguide 20. Each second light guide 20 is connected to a fiber coupler 30 through a second optical switching element 13.

The wavelength-variable femtosecond soliton pulse light source 1 is a femtosecond pulse laser using an Er-doped fiber. A pulse width is preferably 10 to 500 fs. In this example, the pulse width is set to 100 fs, and a pulse interval is set to 20 ns (pulse frequency of 50 MHz). Further, light soliton having a wavelength of 1630 nm is used. Of course, pulse light having a wavelength of about 1 ps may be used instead.

Provided that an effective optical length of the first light waveguide 4 between the optical directional coupler 8 and the fiber coupler 30 is $L_1+L_2$, and the optical fiber 6 has a length L, each reference optical length of the light waveguides 200, 201, ..., and 20n is set to $L_1+L_2+nL$ (n=0, 1, 2, ...). In other words, adjacent waveguides differ in reference optical length by L, that is, the length of the optical fiber 6.

In the case of detecting transmitted light with the above structure of FIG. 2, the first optical switching element 12 and the second optical switching element 13 are switched under control to select the 0th light waveguide 200. In the case of detecting one-time ring down pulse light, the wavelength-variable femtosecond soliton pulse light source 1st light waveguide 201 is selected. Likewise, in the case of detecting n-time ring down pulse light, the nth light waveguide 20n is selected. In this way, each light waveguide is switched under control and an optical length of each light waveguide is effectively changed by oscillation to thereby obtain a synchronous detection waveform as shown in FIG. 1E. Then, an intensity ratio between light pairs is calculated based on the synchronous detection waveform. After that, an attenuation coefficient is determined based on attenuation characteristics of an amplitude for each ring down pulse light. This example enables high-sensitivity detection according to the principle similar to that of the homodyne detection. In practice, its sensitivity was 500 times higher than that of ATR (the minimum detection amount is 1/500).

MODIFIED EXAMPLE

In the above example, the first light waveguide 4 functions as both of an incident waveguide for inputting pulse light to the optical fiber 6 and an output waveguide for outputting ring down pulse light from the optical fiber 6. However, an output light waveguide may be additionally provided to output ring down pulse light through an optical directional coupler separate from the wavelength selective switch 5 of the optical fiber 6. The output light waveguide and the second light waveguide 20 are both connected to the homodyne detector 40 and thus may be designed such that an optical length of the ring down pulse light up to the homodyne detector 40 and an optical length of reference light propagating through the second light waveguide 20 satisfy the above relationship.

In the above example, the optical fiber 6 has a loop shape but may have a linear or curved shape. That is, the linear optical fiber is coupled with the first light waveguide 4 by the wavelength selective switch 5. Then, both ends of the optical fiber are mirror-finished to reflect light. In this case as well, ring down pulse light reciprocating in the linear or curved optical fiber, not the loop one, may be output to the outside to perform synchronous detection of the ring down pulse right and reference light propagated through the second light waveguide having an effective optical length equal to an optical length of the pulse light.

The principle thereof is as above.

According to the present invention, the long optical fiber 6 is used, so a pulse width of the pulse light may not be reduced so much.

A supercontinuum light source may be used as a light source of the present invention. To obtain information in the form of light having a particular wavelength from the supercontinuum light source, each interference waveform (pulse) is subjected to fast Fourier transform to determine an intensity of the particular wavelength of each pulse to get the information based on an attenuation time constant.

EXAMPLE 2

Figure 3:
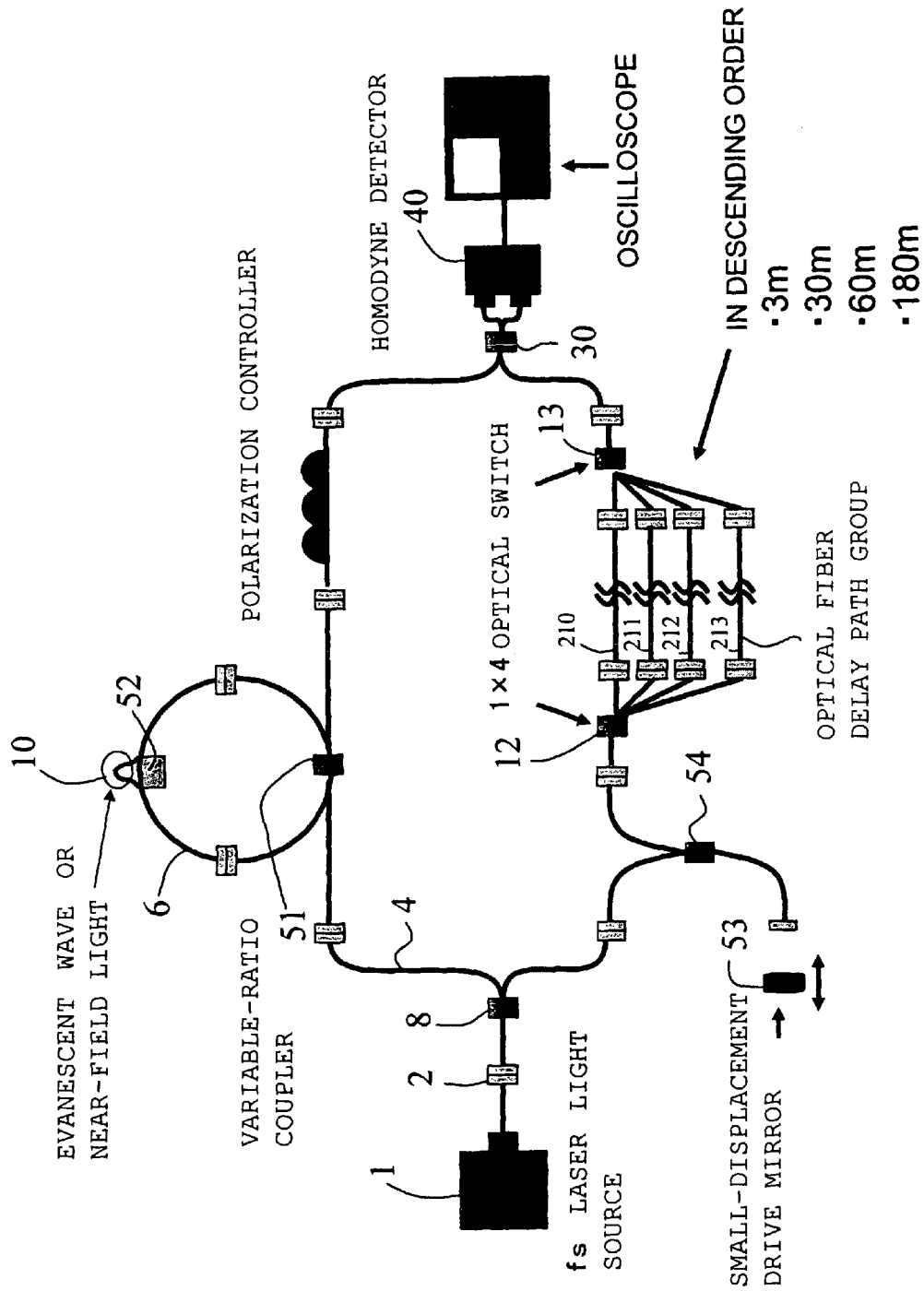
FIG. 3 is a block diagram specifically showing the structure of a ring down spectroscope according to Example 2 of the present invention.

FIG. 3 shows an apparatus according to Example 2. Elements having the same function as those of the apparatus of Example 1 as shown in FIG. 2 are denoted by identical reference numerals. A fs laser light source 1 having a wavelength of 1.55 μm was used, and a length of a loop optical fiber corresponding to the optical fiber 6 of FIG. 2 (corresponding to a cavity) was set to 3 m. A laser from the fs laser light source 1 is split into the first light waveguide 4 and fiber delay lines 210 to 213 by the optical directional coupler 8. The laser split to the optical fiber delay line side is incident on a drive mirror 53 that can be displaced with a small range through an optical directional coupler 54. The laser reflected by the mirror 53 is incident on the optical fiber delay lines 210 to 213 through the optical directional coupler 54. The drive mirror 53 has the same function as the piezoelectric tube scanners 15 of Example 1. The mirror oscillates an optical path of the laser with a small width. The optical fiber delay lines 210 to 213 are each made up of fibers having an optical path of 3, 30, 60, and 180 m, respectively. Optical switches 12 and 13 switch the lines to select an arbitrary optical fiber delay line. A wavelength of interference between the laser propagating through the optical fiber delay lines 210 to 213 and the ring down light output from the optical fiber 6 is detected with the balanced homodyne detector 40. In FIG. 2, the loop fiber 6 is coupled with the optical switch 5. In this example, a variable-ratio coupler 51 is used. As a head portion 52 for measuring a sample is provided by polishing the optical fiber near to its core. The head 52 enables measurement of an absorptance of the sample such that an evanescent wave of light propagated in the optical fiber 6 or near-field light mutually reacts with the sample.

Figure 4:
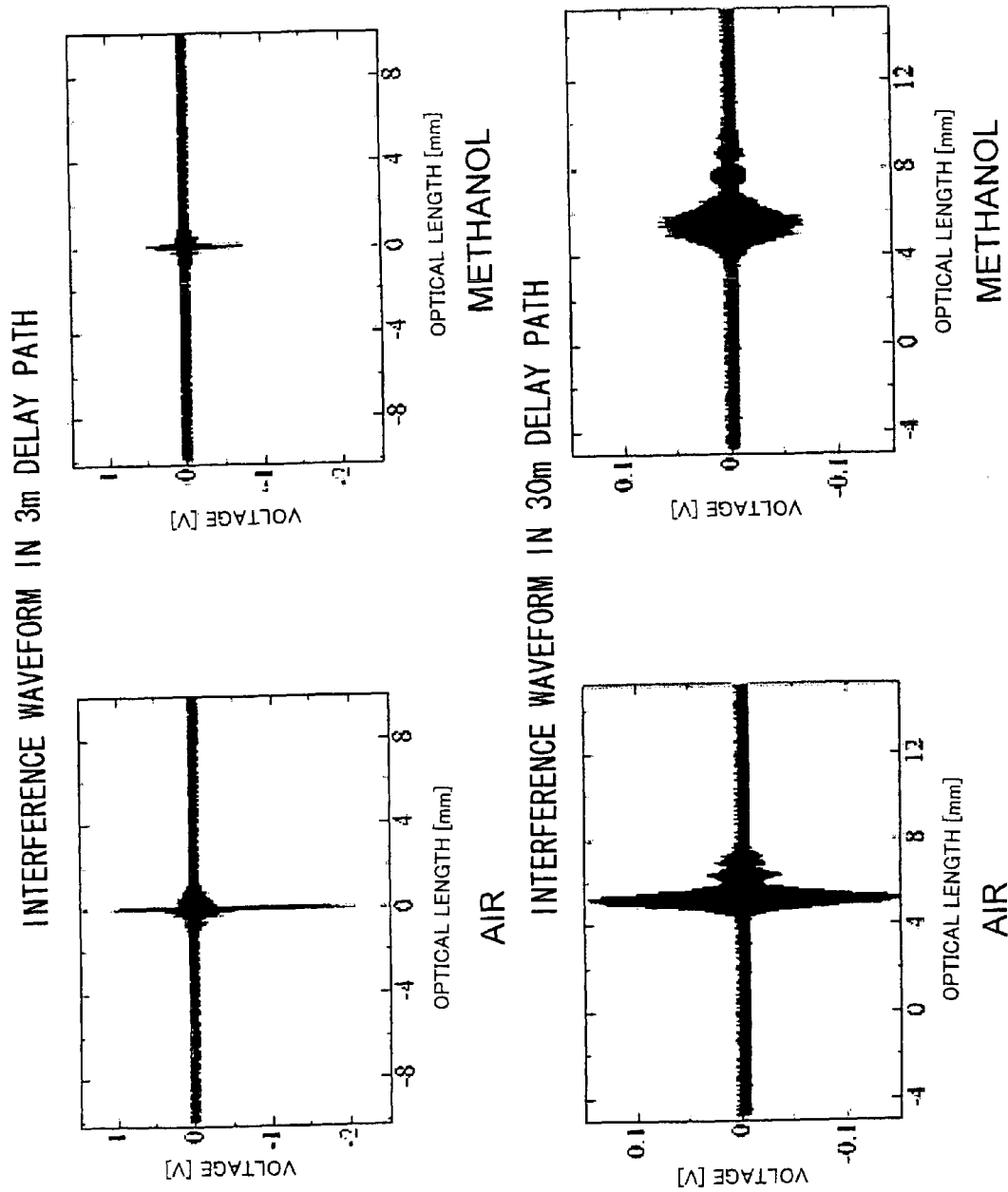
FIG. 4 is a measurement chart showing an interference wavelength obtained by measuring light absorptance of the air and ethanol with a delay path length being set to 3 m and 30 m based on the spectroscope of Example 2.
Figure 5:
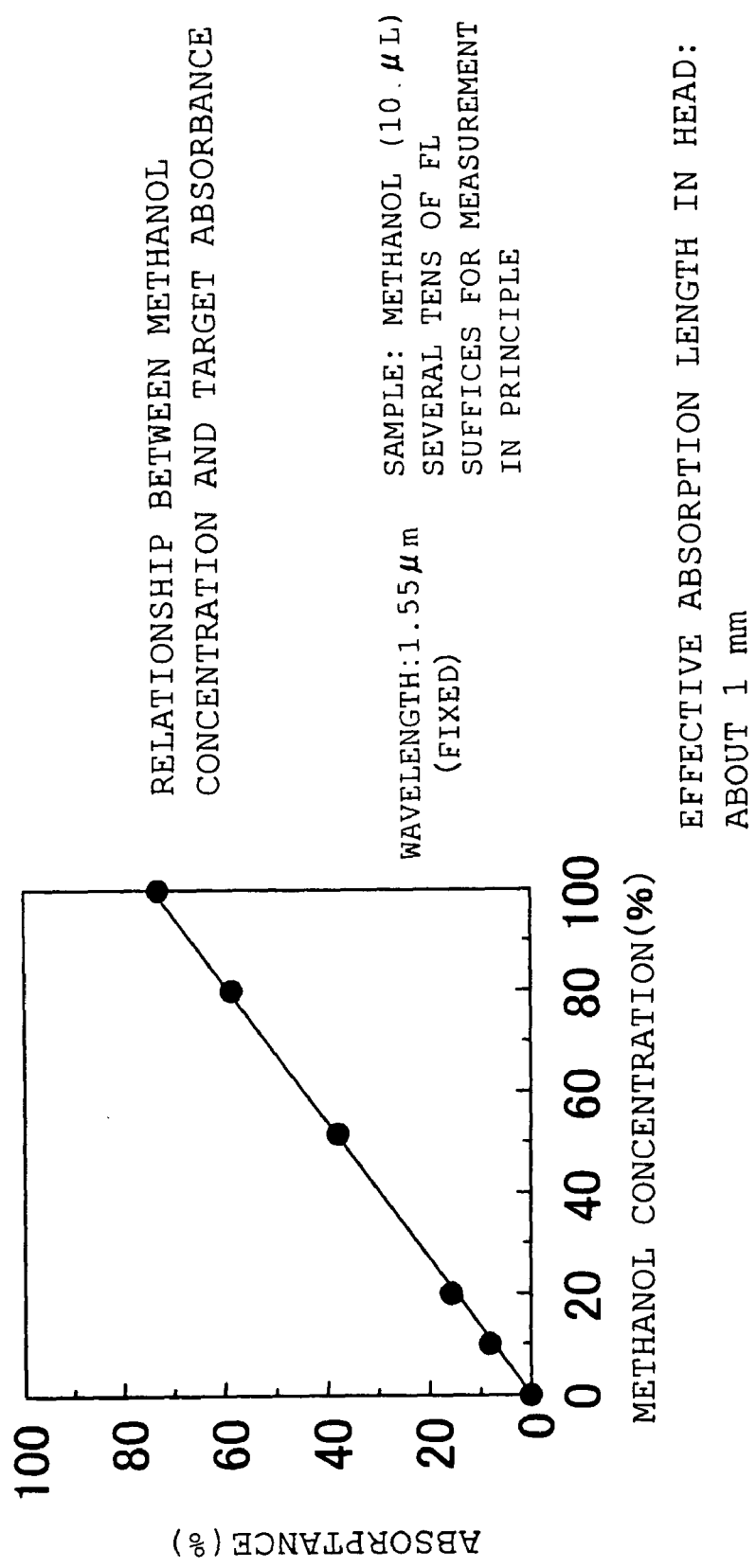
FIG. 5 is a measurement chart showing absorptance characteristics relative to a methanol concentration at the time of measuring the absorptance of methanol with varying concentrations based on the spectroscope of Example 2.

FIG. 4 shows interference waveforms in the 3 m optical fiber delay line and the 30 m optical fiber delay line. As the sample, pure water and methanol were used. As understood from FIG. 4, methanol involves lower interference intensity and higher absorptance than pure water in either the 3 m line or the 30 m line. FIG. 5 shows a change in absorptance derived from the interference intensity with varying methanol concentration under such a condition that the 30 m optical fiber delay line is used. 10 μL of the methanol as a sample was dropped to the head portion 52 for measurement. In this case, the head portion 52 has an effective optical length of about 1 mm. If the sample is methanol having a relatively large absorption coefficient of 2 $cm^{-1}$ (with a wavelength of 1.55 μm), it would be understood that a small amount of sample, for example, 2 fL, suffices for satisfactory measurement in calculation.

Further, since methanol has a relatively large absorption coefficient, a large absorption coefficient could be measured even with the 30 m optical fiber delay line that is 10 times longer than an optical fiber corresponding to a cavity. In the case of using methanol, 2 fL of methanol having a concentration of 3 ppm can be measured with an optical fiber delay line having a length of about 2 km in calculation.

As for a sample having a small absorption coefficient, high absorbance is not measured, so it is necessary to perform measurement with a longer optical fiber delay line in order to increase sensitivity.

If optical fiber delay lines of different optical lengths are switched for the measurement, it is possible to measure even a high-concentration sample and a sample having a very low concentration. In the case of using a wavelength-variable soliton pulse light source, an absorption coefficient can be measured over a wavelength range of about 1 µm to about 2 µm.

Second Embodiment

Provided that L represents an optical length of an optical path between two mirrors constituting a cavity, a difference in optical length between ring down pulse lights is 2 L. If c represents light velocity, a time interval between adjacent ring down pulse rights is 2 L/c. That is, as shown in FIG. 1A, light pulses output from the cavity include transmitted lights $S_1$, $S_2$, $S_2$, $S_4$, . . . , which are not reflected by the mirrors. Then, ring down lights are output in order at intervals of 2 L/c as follows. That is, one-time ring down pulse light $L_{11}$ that is reflected once by the two mirrors is output with a delay of 2 L/c from the arrival of the transmitted light $S_1$. Then, two-time ring down pulse light $L_{12}$ that is reflected twice by the two mirrors is output with a delay of 2 L/c from the arrival of the ring down pulse light $L_{11}$. The same applies to the transmitted lights $S_2$, $S_2$, and $S_4$. If the optical length L of the optical path between the two mirrors and a pulse interval $T_P$ are adjusted, a pair of ring down pulse lights following one transmitted light can be prevented from overlapping the next transmitted light with ease. Hereinafter, the transmitted light (pulse light not absorbed to the sample) and the ring down pulse lights are referred to as signal light.

On the other hand, reference light (reference) passed through another path, and the pulse of the transmitted light and subsequent ring down light pair as signal light are subjected to homodyne detection. If an optical path length of the reference light is completely equal to that of the transmitted light, a pulse detected through the homodyne detection of the transmitted light based on the reference light matches a pulse of the reference light. This detection output is represented by A. Next, if an optical path length of the reference light is completely equal to that of one-time ring down light, a pulse detected through the homodyne detection of the transmitted light based on the reference light also matches a pulse of the reference light. This detection output is represented by αA (0<α<1). Likewise, if an optical path length of the reference light is completely equal to that of n-time ring down pulse light, a pulse detected through the homodyne detection of the transmitted light based on the reference light also matches a pulse of the reference light. At this time, the detection output of $\alpha^n A (0<\alpha<1)$ is obtained.

However, it is difficult to completely match an optical path length of the reference light with an optical length of the transmitted light and each ring down pulse light. This is because signal light having a short pulse width is used. To that end, a movable mirror that can oscillate is provided in the optical path of the reference light. As a result, adjacent pulses of the reference light travel different optical lengths due to oscillations of the movable mirror. A pulse interval of the reference light reflected by the mirror becomes longer or shorter than before. At this time, if an amplitude a of the movable mirror is set shorter than the optical length L between two mirrors constituting a cavity, a change 2 a/c in pulse incident time due to change in pulse interval of the reference light can be smaller than the time interval 2 L/c between the adjacent ring down pulse lights. In this way, an optical length of the reference light split from signal light having a given pulse frequency (pulse interval) is adjusted by oscillation with the oscillating movable mirror to thereby achieve the reference light having an optical length almost equal to the optical length of the transmitted light and each ring down pulse light.

In this embodiment as well, referring to FIG. 1B etc., interference between two pulse trains of this embodiment is described based on the same principle as in the first embodiment using concrete numeric values. The signal light is pulse light having a pulse width of 100 fs ($1 \times 10^{-13}$ seconds) and a pulse interval of $2 \times 10^{-8}$ seconds (pulse frequency of 50 MHz). The oscillation frequency of the mirror inserted to the optical path of the reference light is set to 20 Hz. The optical length of the reference light is equal to the optical length of the transmitted light at the center of oscillation of the mirror. The mirror can oscillate by ±4 mm.

Provided that the center of oscillation of the mirror is x (mm) at time t (sec), and x=0 when t=0, x=4 sin 40πt. A mirror velocity v (mm/sec) is calculated as follows: v=160π cos 40πt, and thus, v=500 mm/sec at t=0. As a result, the mirror moved by $1 \times 10^{-8}$ m before the two pulses of the reference light having the pulse interval of $2 \times 10^{-8}$ seconds, so an optical length difference is $2 \times 10^{-8}$ m. This means that a pulse interval of the reference light reflected by the mirror becomes longer or shorter than that of the reference light before reflection by $6.67 \times 10^{-17}$ seconds.

Then, if the 0th pulse of the signal light and that of the reflected reference light are output with a difference of a pulse width of $1 \times 10^{-13}$ seconds, and the pulse of the reflected reference light is input ahead of that of the signal light with a pulse interval longer than that of the signal light by $6.67 \times 10^{-17}$ seconds as shown in FIG. 1B, for example, $1 \times 10^{-13}$ sec/$6.67 \times 10^{-17}$ sec=1500, so a pulse of the signal light matches a pulse of the reflected reference light at a 1500th pulse. A delay corresponding to a pulse width of $1 \times 10^{-13}$ seconds occurs between the signal light and the reflected reference light at a 3000th pulse. At this time, the pulse of the reflected reference light is input later than that of the signal light. A pulse interval of the signal light is $2 \times 10^{-8}$ seconds, so a time interval between the 0th pulse and the 3000th pulse is $6 \times 10^{-5}$ seconds.

In the case of brining about interference between the signal light and the reflected reference light and performing homodyne detection thereof, the detection output of FIG. 1C is obtained. The signal light interferes with the reflected reference light during the 3000 pulses under the condition of FIG. 1B. The detection output is just 0 at the 0th pulse, maximum at the 1500th pulse, and just 0 at the 3000th pulse. During this period, 2999 peaks appear under the envelop (as indicated by the dotted line) of FIG. 1C. The envelop and 2999 peaks under the envelop appear for $6 \times 10^{-5}$ seconds and then disappear till 0.05 seconds later; after the elapse of 0.05 seconds, the mirror is returned to the original position. That is, the envelop and 3000 peaks within the envelop appear for $6 \times 10^{-5}$ seconds at intervals of 0.05 seconds. Otherwise these disappear.

Considering this phenomenon from a microscopic angle, very sharp peaks appear with a width of $6 \times 10^{-5}$ seconds at intervals of 0.05 seconds (see FIG. 1D). The same applies to other pulse waveforms, not a rectangular waveform of FIG. 1B. As for a difference in interference degree between the 1500th pulse and pulses adjacent to the 1500th pulse as shown in FIG. 1B, one pulse includes 18.4 wave lengths and the phase difference between the adjacent two pulses is as small as $2\pi/80$ at the wavelength of 1.63 for example. In this case, an intensity of interference in plural pairs of signal light and reflected reference light at around any peak of the envelope is substantially equal to that at the peak of the envelop. Thus, it is unnecessary to completely match pulse phases of the signal light and the reflected reference light. Further, it is unnecessary to adjust the center of oscillation of the mirror to exactly match a reference optical length of the reference light reflected by the mirror with an optical length of the signal light. That is, the optical length of the signal light only has to match the optical length of the reflected reference light at any point within a movable range of the mirror. Thus, pulse trains having a much higher pulse frequency than the oscillation frequency of the mirror and amplitude can be guided to a reference light path to thereby facilitate homodyne detection of the reference light and the signal light.

As described above, these optical lengths only need to substantially match each other. Thus, homodyne detection can be performed with ease under such condition that the "optical lengths match each other during the oscillation" at several points even if the oscillating mirror is moved in the optical path direction. If the oscillation center of the oscillating mirror is moved to a position where the optical length of the reference light matches that of the transmitted lights $S_1$, $S_2$, $S_2$, $S_4$, ... of FIG. 1A, a position where the optical length of the reference light matches that of the one-time ring down pulse lights $L_{11}$, $L_{21}$, $L_{31}$, $L_{41}$, ... of FIG. 1A, a position where the optical length of the reference light matches that of the two-time ring down pulse lights $L_{12}$, $L_{22}$, $L_{32}$, $L_{42}$, ... of FIG. 1A, and a position where the optical length of the reference light matches that of the n-time ring down pulse lights $L_{1n}$, $L_{2n}$, $L_{3n}$, $L_{4n}$, ... of FIG. 1A, as shown in FIG. 1E, interference with the transmitted light, interference with the one-time ring down pulse light, interference with of the two-time ring down pulse light, and interference with the n-time ring down pulse light can be measured as plural very-sharp peak groups with a width of $6 \times 10^{-5}$ seconds.

EXAMPLE 3

Figure 6:
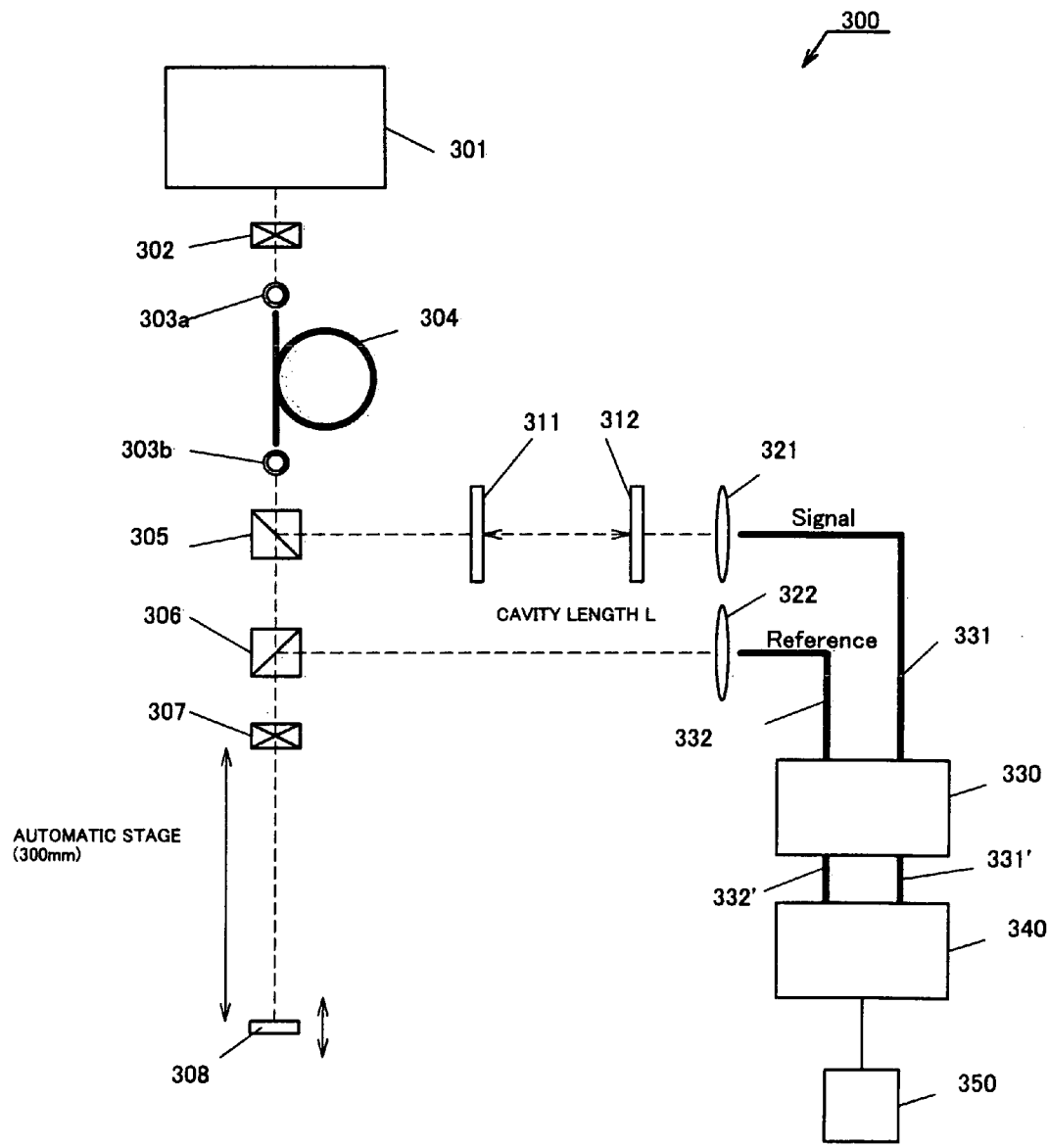
FIG. 6 is a block diagram specifically showing the structure of a cavity ring down spectroscope 300 according to Example 3 of the present invention.

FIG. 6 is a block diagram showing the structure of a cavity ring down spectroscope 300 according to an example of the present invention. The cavity ring down spectroscope 300 includes a wavelength-variable femtosecond soliton pulse light source 301, a ½-wavelength plate 302, a sphere lens 303a, a polarization maintaining fiber 304, a sphere lens 303b, a beam splitter (light split means) 305, a polarizing beam splitter 306, a ¼-wavelength plate 307, and a galvano mirror 308 capable of changing its position and oscillating. Signal light (signal light) is guided to high-reflection mirrors 311 and 312 through the wavelength-variable femtosecond soliton pulse light source 301, the wavelength-variable femtosecond soliton pulse light source ½-wavelength plate 302, the sphere lens 303a, the polarization maintaining fiber 304, and the sphere lens 303b, and ring down light reaches a biconvex lens 321. At the same time, reference light (reference light) similarly reaches the beam splitter 305, passes through the polarizing beam splitter 306 and the wavelength-variable femtosecond soliton pulse light source ¼-wavelength plate 307, and is then reflected by the galvano mirror 308 capable of changing its position and oscillating. The reflected light enters the biconvex lens 322 from the polarizing beam splitter 306 through the wavelength-variable femtosecond soliton pulse light source ¼-wavelength plate. The signal light incident on the biconvex lens 321 and the reference light incident on the biconvex lens 321 are both guided to a fiber coupler 303 through an optical fiber 331 and an optical fiber 332, and then guided to a balanced detector 340 (homodyne detection means) through optical fibers 331' and 332', respectively. An electric signal output from the balanced detector 340 is A/D-converted and analyzed with a digital processor 350.

The wavelength-variable femtosecond soliton pulse light source 301 of the cavity ring down spectroscope 300 is a femtosecond pulse laser using an Er-doped fiber. A pulse width is preferably 10 to 500 fs. In this example, the pulse width is set to 100 fs, and a pulse interval is set to 20 ns (pulse frequency of 50 MHz). Further, light soliton having a wavelength of 1630 nm is used.

The galvano mirror 308 oscillates in a vertical direction in figure plane with the total width of 8 mm at a frequency of 20 Hz. Under such condition, the galvano mirror 308 can move 300 mm downwardly in figure plane.

Cavity regions defined by the high-reflection mirrors 311 and 312 have a cavity length of 35 mm and 46 mm. The high-reflection mirrors 311 and 312 each have a reflectivity of 99.8% or higher. A waveform of FIG. 1E is detected with the above structure of FIG. 6. Then, an intensity ratio between light pairs is calculated. Further, a difference between an output time of the signal light as signal light and an output time of each n-time ring down light is additionally calculated. In this way, intensity of each n-time ring down light relative to the transmitted light is plotted with respect to the time difference between the transmitted light and the n-time ring down light to determine an absorption coefficient of a sample set in the cavity based on a time constant.

Figure 8:
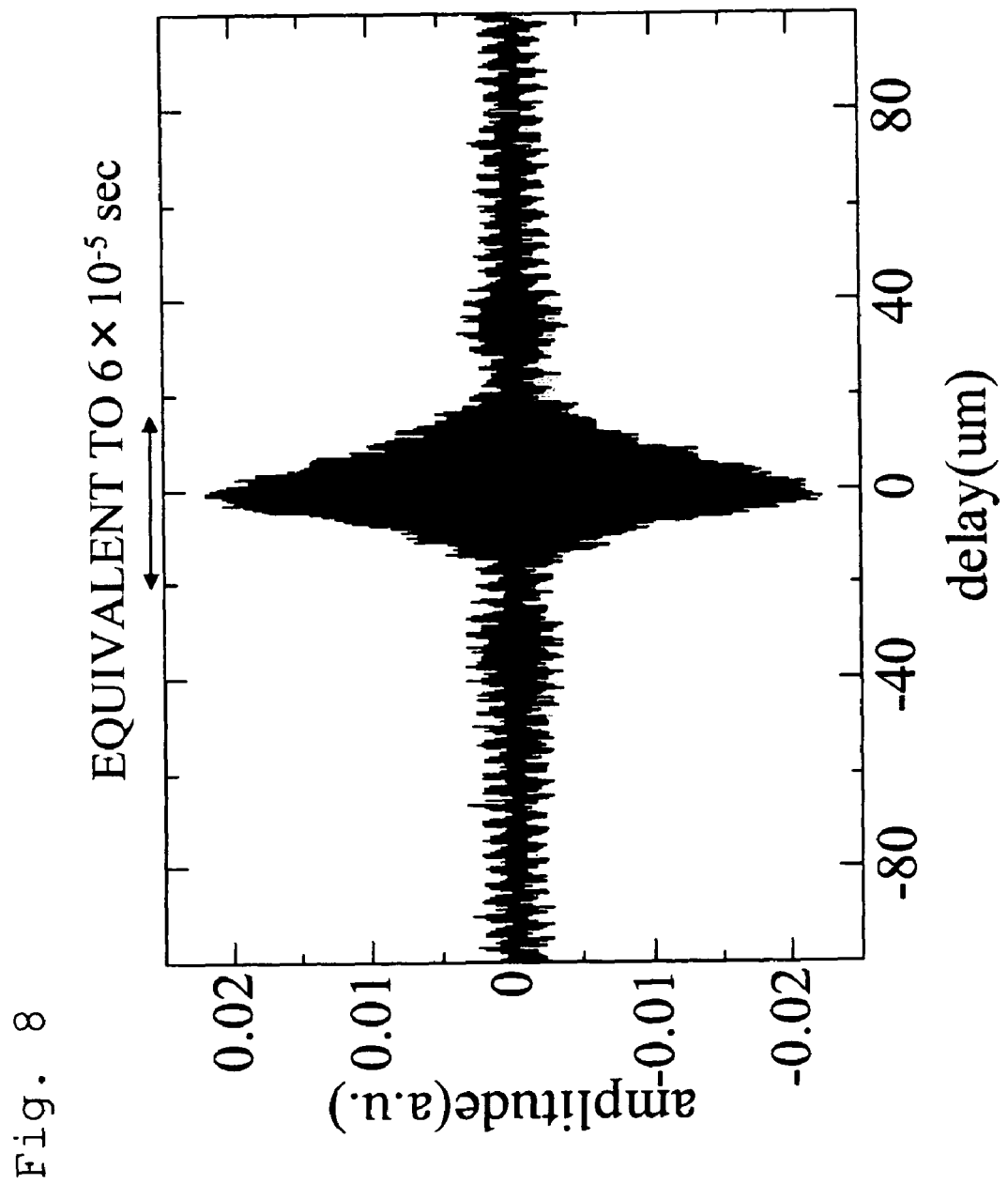
FIG. 8 is a characteristic diagram showing an interference wavelength of laser, which is obtained with an apparatus of Example 3 as shown in FIG. 6.

FIG. 8 shows an actual waveform data obtained with the structure of FIG. 6. This waveform is an interference waveform obtained before the envelop is selected. In this case, a response speed of a photodetector is as low as 1 kHz, so a pulse train having a pulse width of $6 \times 10^{-5}$ seconds as shown in FIG. 1E is observed as one bit interference pulse waveform. If a balanced homodyne detector using a photodetector that achieves a higher-speed response is used, a waveform can be measured like the waveform of FIG. 1E.

This example enables high-sensitivity detection based on the same principle as the homodyne detection. In practice, its sensitivity was 500 times higher than that of ATR (the minimum detection amount is 1/500).

FIG. 7 is a diagram showing three methods for setting a substrate on which a sample is attached in a cavity region.

The first method is to allow transmission of infrared light through a substrate (Sub) having a sample (Obj) attached thereonto as shown in FIG. 7A. In this case, the substrate needs to transmit the infrared light enough. In addition, it is important to facilitate adjustment of an absorption coefficient and a substrate thickness.

The second method is such that the infrared light is reflected at an interface of the substrate (Sub) having a sample (Obj) attached thereonto as shown in FIG. 7B. In this case, the substrate should have high reflectivity to the infrared light. It is unnecessary to adjust the substrate thickness.

The third method is such that a sample is attached to a side surface A of a prism (priz) having the isosceles trapezoidal bottom surface, which corresponds to the base of the isosceles trapezoidal bottom surface, the infrared light is guided from a side surface B corresponding to the side of the isosceles trapezoidal bottom surface and reflected at the interface between the side surface A of the prism and the sample attached thereto, and then, the light is transmitted through a side surface C corresponding to the side of the isosceles trapezoidal bottom surface, which is opposite to the side surface B. This method is based on the phenomenon that the sample (Obj) absorbs an evanescent wave at around the reflection point. Moreover, it is possible to provide the high-reflection mirror 11 to the side surface B and the high-reflection mirror 312 to the side surface C to set a cavity to an inner portion of the prism (Priz) only.

Figure 9:
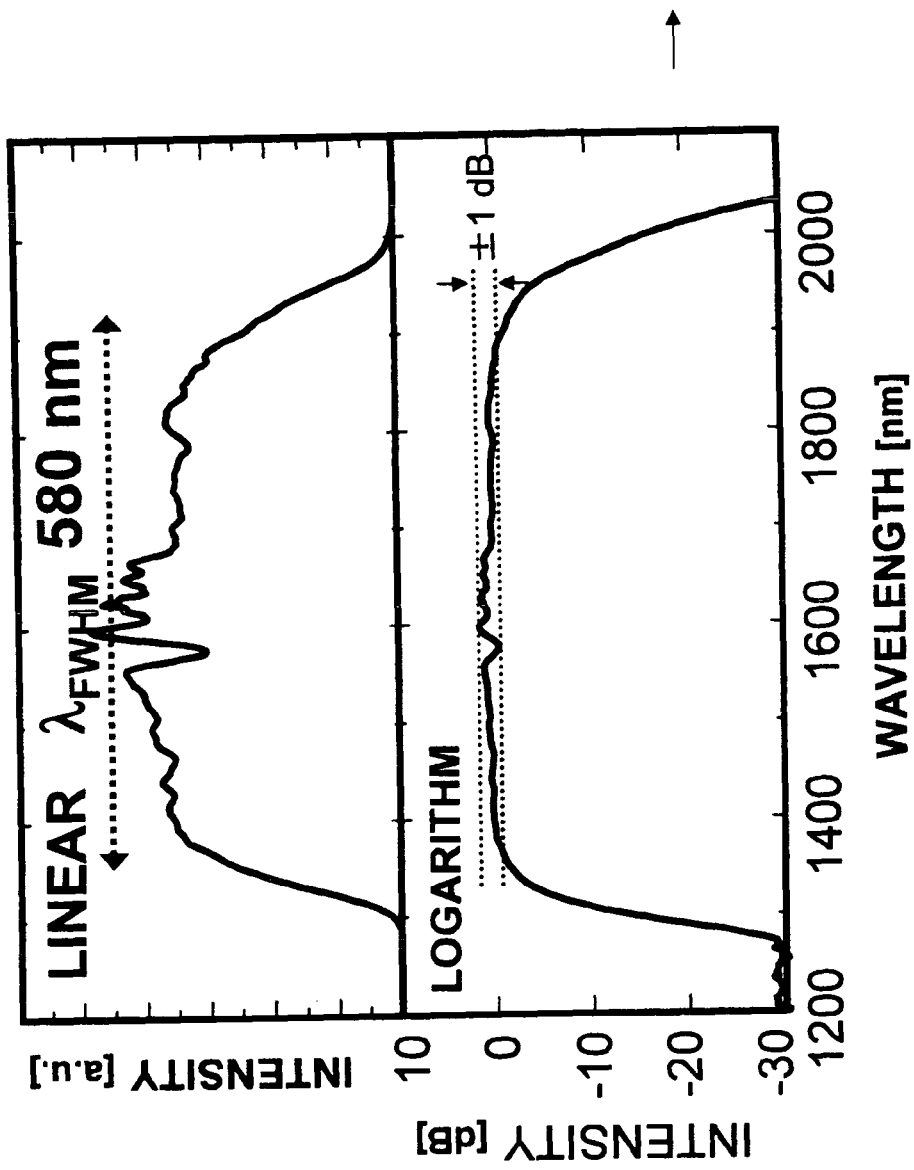
FIG. 9 is a characteristic diagram showing a spectrum of supercontinuum light used in the apparatus of Example 3.
Figure 10:
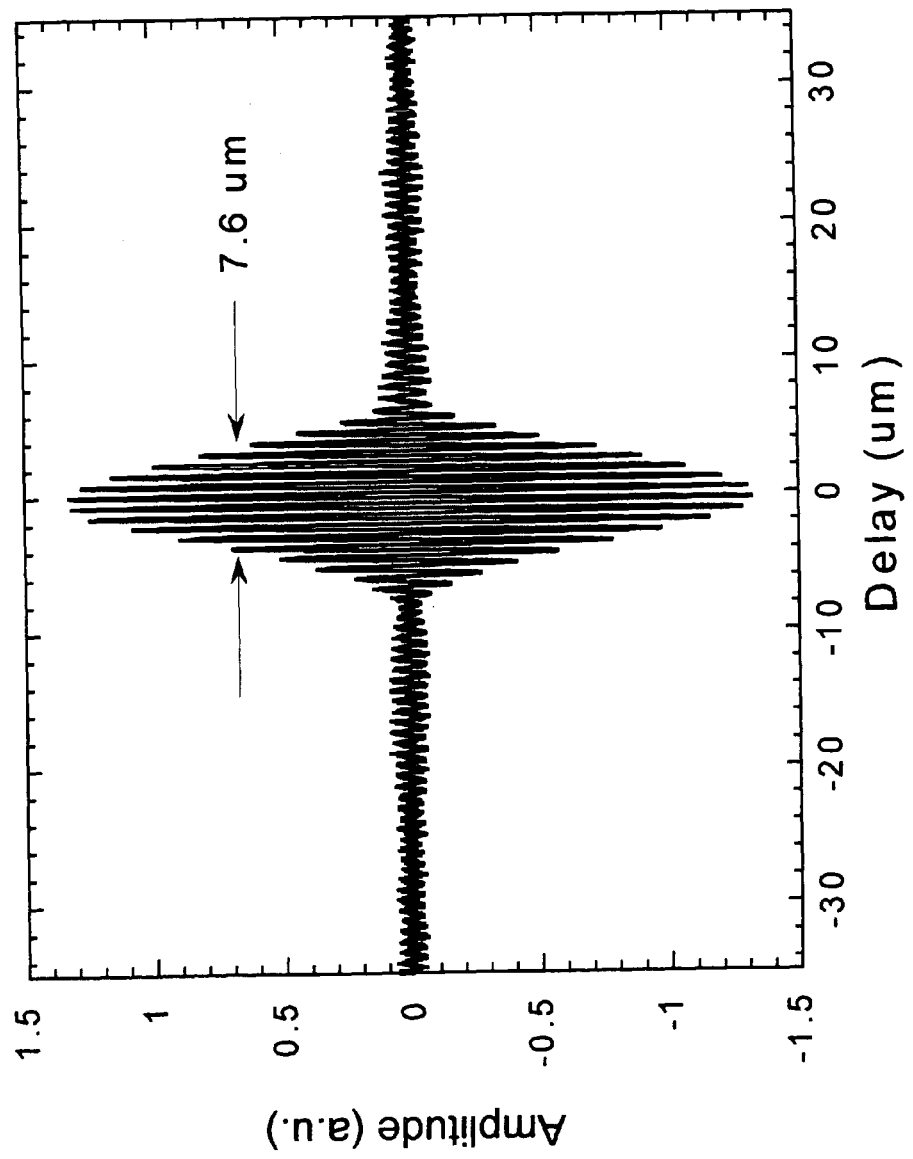
FIG. 10 is a characteristic diagram showing an interference wavelength of laser in the case of using supercontinuum light having the spectrum of FIG. 9 in the apparatus of Example 3

A supercontinuum light source having a spectrum of FIG. 9 may be used as the light source of the present invention. FIG. 10 shows an interference waveform obtained with similar structure to that of FIG. 6 by use of the light source. To determine an absorption coefficient at a particular wavelength based on the interference waveform, each interference waveform (pulse) is subjected to fast Fourier transform to determine an intensity of the particular wavelength of each pulse to calculate the coefficient based on an attenuation time constant.

Third Embodiment

The present invention is described by way of examples but is not limited to the following examples.

EXAMPLE 4

Figure 11:
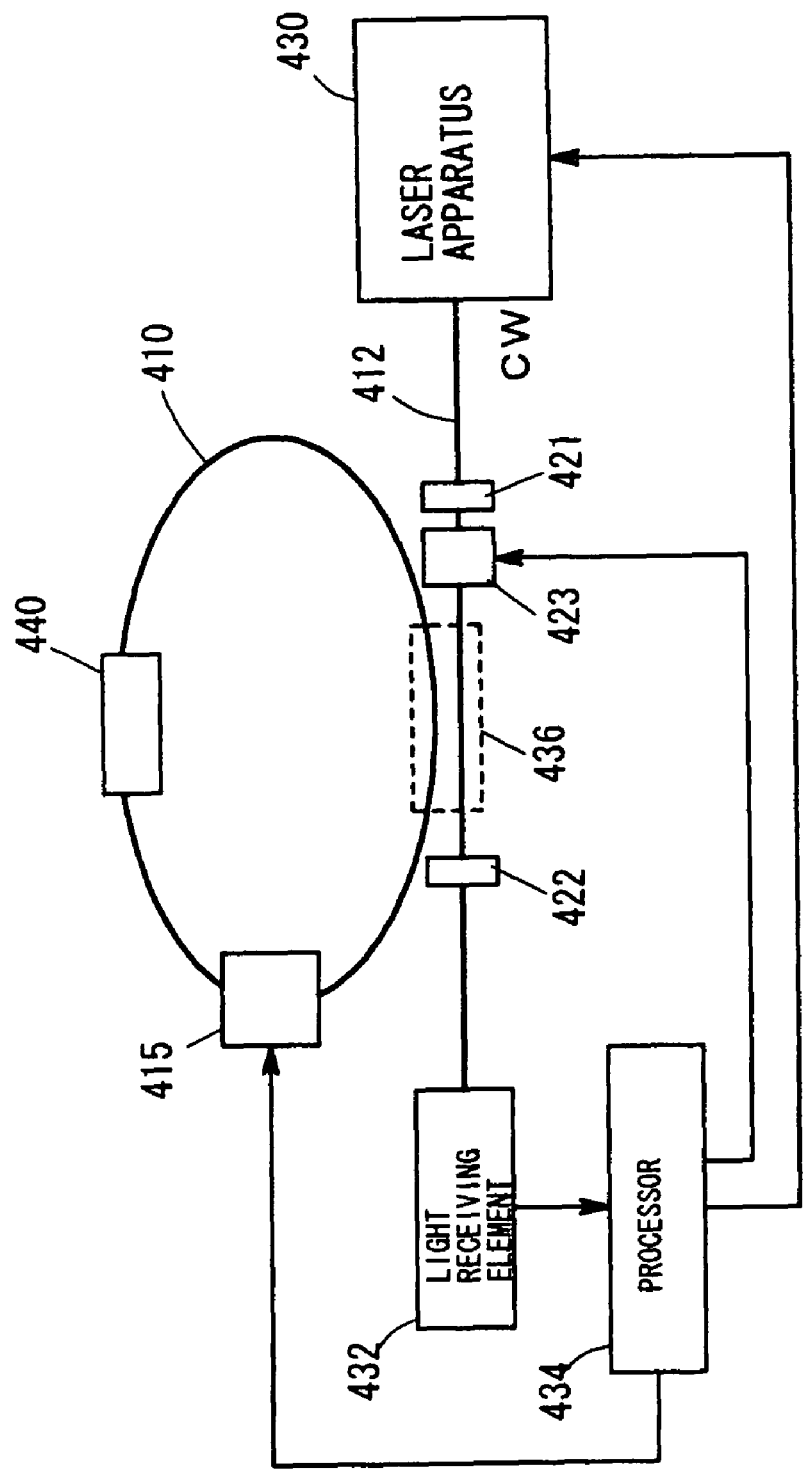
FIG. 11 is a diagram specifically showing an apparatus according to Example 4 of the present invention.

As shown in FIG. 11, a first light waveguide 412 for guiding light is optically coupled with a loop optical fiber 410 by way of an optical directional coupling element 436. A sample 440 is inserted to the light waveguide of the loop optical fiber 410. The optical fiber 410 is cut and its end faces are set face to face. The sample 440 is inserted to a space between the end faces. The apparatus is designed such that light passes through the sample 440. Further, the optical fiber 410 is provided with an optical amplifying element 415. The first light waveguide 412 is made up of an optical fiber, which has one end connected to a laser device 430 capable of outputting continuous laser light and the other end connected to a detection element 432 and a processor 434 that controls an amplification factor not to attenuate ring down pulse light input to the detection element 432 to calculate absorption characteristics of the sample based on the amplification factor.

Further, the first light waveguide 412 is provided with an optical directional coupling element 436 for optically coupling the loop optical fiber 410 with the first light waveguide 412. A second polarizer 421 is provided on the laser light incident side of the optical directional coupling element 436, and a first polarizer 422 is provided on the laser light incident side of the detection element 432. A faraday rotator 423 as a polarization control element is provided on the laser light incident side of the optical directional coupling element 436. The second polarizer 421 is an element for outputting only S-polarized light components, for example. The faraday rotator 423 is an element for applying a magnetic field in the waveguide direction to rotate a polarized light phase by 90 degrees to thereby turn S-polarized light to P-polarized light, for example, in response to controls signals from the processor 434. The optical directional coupling element 436 splits only P-polarized light to the optical fiber 410 in the travelling direction alone. The first polarizer 422 transmits light polarized to a predetermined direction, for example, P-polarized light only.

Continuous laser light output from the laser device 430 enters the second polarizer 421 to output only S-polarized light components to the first light waveguide 412. The S-polarized continuous laser light passes through the faraday rotator 423 not applied with the magnetic field and then enters the optical directional coupling element 436. Here, the optical directional coupling element 436 splits only P-polarized light to the optical fiber 410. Thus, no laser light is output to the optical fiber 410 in this state. The S-polarized continuous laser light passed through the optical directional coupling element 436 enters the first polarizer 422. However, the first polarizer 422 transmits P-polarized light alone, so the S-polarized continuous laser light does not enter the detection element 432. Hence, there is no fear of the continuous laser light being output from the laser device 430 and incident on the detection element 432 and no fear of hindering the detection element 432 from receiving ring down pulse light.

If a pulse magnetic field is applied to the faraday rotator 423 in response to a pulse control signal output from the processor 434, a phase of laser light passing through the faraday rotator 423 is rotated and turned into P-polarized light from S-polarized light during this period only. That is, the faraday rotator 423 outputs P-polarized pulse light. If no field is applied, the rotator outputs continuous S-polarized light. The P-polarized pulse laser light enters the optical directional coupling element 436 and split to the optical fiber 410, and then circulates in the optical fiber 410 clockwise in the figure. A sample absorbs light at every turn, and the P-polarized pulse laser light amplitude is sequentially reduced. That is, P-polarized ring down pulse light is obtained. The ring down pulse light is partially split to the first light waveguide 412 side through the optical directional coupling element 436 at every turn. The light is partially split to the first light waveguide 412 side through the optical directional coupling element 436 and incident on the first polarizer 422 because of the P-polarized light. The first polarizer 422 transmits P-polarized light only. Thus, the ring down pulse light is incident on the detection element 432.

The processor 434 controls an amplification factor of the optical amplifying element 415 not to attenuate an amplitude of the ring down pulse light detected with the detection element 432. Thus, if an absorption coefficient of the sample and an amplification factor become equal, the amplifying element amplifies the light beforehand by an attenuation amount of light in the sample, so the pulse light passed through the sample can be kept from attenuating. That is, a pulse train amplitude is not changed. At this time, the optical amplifying element 415 only needs to have an amplification factor enough to cope with a change of sample's absorption coefficient with time. The measurement is executed with varying wavelengths of the continuous laser light to thereby determine wavelength absorptance characteristics of the sample and identify atomic and molecular structures of the sample. In this case, an absorption coefficient can be measured under such condition that an amplitude of light incident to the sample is kept constant. Thus, it is possible to eliminate a non-linear effect and measure the absorptance coefficient relative to light intensity with accuracy. In other words, non-linear characteristics of the absorptance coefficients of the sample can be determined if the above measurement is executed with varying intensities of laser light.

In addition, since a measurement system itself attenuates, in practice, ring down light of P-polarized pulse laser light is measured under such condition that no sample is set, and an amplification factor of the amplifying element is controlled similar to the above process not to attenuate the ring down light. Then, an attenuation degree of the measurement system can be measured based on the amplification factor. The absorptance coefficient of the sample measured as above is corrected based on the attenuation degree of the measurement system to thereby obtain a correct absorptance of the sample. Therefore, the absorptance can be measured with high accuracy.

Ring down characteristics of the P-polarized pulse laser light are measured and plotted with the horizontal axis representing the number of ring down processes and the vertical axis representing an amplitude of the ring down pulse light. As for the characteristics, an amplification factor of the amplifying element may be slightly adjusted, and fed back not to attenuate an amplitude of the ring down pulse light.

In the above example, the optical directional coupling element 436 is well known. The optical directional coupling element can guide the ring down pulse light of laser light from the optical fiber 410 to the detection element 432. Further, if its coupling factor is changed, intensity of light circulating in the optical fiber 410 can be adjusted. As a result, an attenuation degree of light input to the detection element 432 can be adjusted, so an attenuation coefficient can be measured with the same dynamic range. Hence, measurement accuracy can be improved.

In the above example, the laser device 430 is a continuous oscillation laser. However, a pulse oscillation laser may be used instead, and the first polarizer 422, the second polarizer 421, and the faraday rotator 423 can be omitted. In this case, pulse laser light can be incident on the optical fiber from the first light waveguide 412 through the optical directional coupling element 436.

EXAMPLE 5

Figure 12:
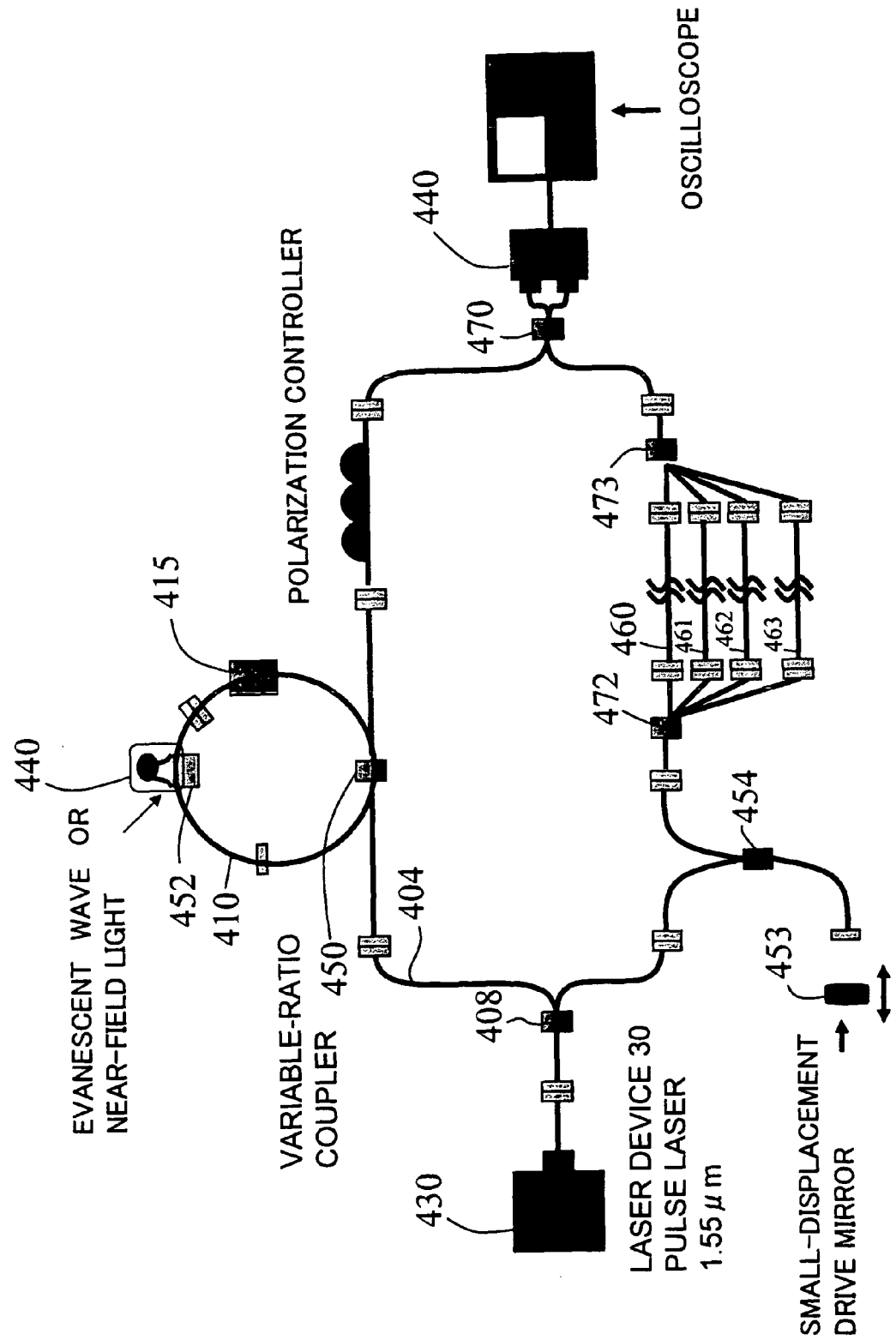
FIG. 12 is a diagram specifically showing an apparatus according to Example 5 of the present invention.

An apparatus of this example is the same as that of Example 2 as shown in FIG. 3 except that a semiconductor optical amplifier is provided to the optical fiber 6. FIG. 12 shows the apparatus structure. In FIG. 12, the structure regarding the light waveguide 412, the loop optical fiber 410, an insertion position of the sample 440, the detection element 432, and the processor 434 is the same as Example 4. A pulse laser is used for the laser device 430, and the first polarizer 422, the second polarizer 421, and the faraday rotator 423 are omitted.

In this example, a semiconductor laser 430 having a wavelength of 1.55 μm is used as a pulse laser. The laser performs pulse oscillation through current modulation. To obtain the ring down pulse light at a high S/N ratio, the balanced homodyne detector 440 is used. Thus, as in the apparatus of Example 2 as shown in FIG. 3 unlike Example 4, light of pulse laser is split into two by a 1×2 optical directional coupler 408. One of the two lights is guided to the loop optical fiber 410 by way of the first light waveguide 404 through a variable-ratio coupler 450 similar to Example 4 while the other light is guided to a optical fiber delay lines 460 to 463 as a reference signal for homodyne detection.

At an insertion position of the sample 440, the side portions of the optical fiber are polished near to the core, and a head 452 is provided, which causes mutual reaction between an evanescent wave of light propagated in the fiber or near-field light with the sample. After propagating from the head 452 provided to the optical fiber 420 and mutually reacting (absorbed) with the sample through the variable-ratio coupler 450, the signal light is guided to a 2×1 optical directional coupler 470. Reference light passes through one of 4 optical fiber delay lines of different lengths through a 1×4 optical switch 472 and enters a 2×1 optical directional coupler 470 through a 4×1 optical switch 473. The signal light and reference light guided to the optical directional coupler 470 interfere with each other when an optical length of the reference light is almost equal to an integral multiple of that of the loop path length. Thus, a drive mirror 453 that allows small displacement is inserted. If the mirror 453 is driven, an interference waveform is input to the homodyne detector and measured with a high S/N ratio. The other structure is the same as that of FIG. 3.

An amplifying element 415 is inserted to the loop optical fiber 410. In this example, a semiconductor optical amplifier (SOA) 415 was used. This amplifying element 415 is not limited to the SOA but may be an optical fiber amplifier made of rare earth element such as Er. In the case of using a high-power laser such as a fs laser, the SOA is not suitable for amplification, so an optical fiber amplifier is preferred.

Figure 13:
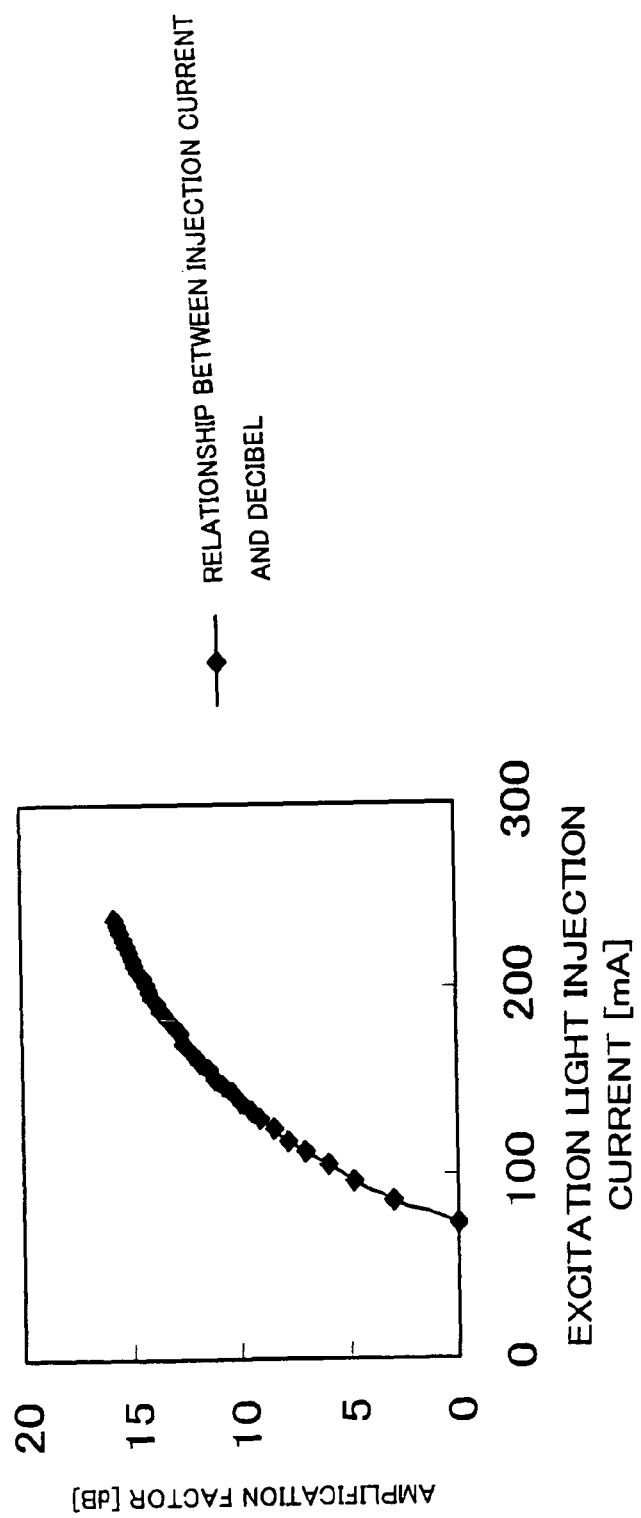
FIG. 13 is a characteristic chart showing a result of measuring an amplification factor of a semiconductor optical amplifier used in an apparatus of Example 5 in the case where an amount of current applied to a power source of the semiconductor optical amplifier.

FIG. 13 shows a result of measuring an amplification factor of the SOA with varying amounts of current supplied to an SOA power source. As apparent from FIG. 13, the SOA can amplify a signal by about 16 dB. FIG. 14A shows signal intensity obtained with varying delay optical lengths of the optical fiber, 30 m, 60 m, and 180 m, if an amplification factor of the SOA is set to 0 dB (amplification factor of 1). The black circle of FIG. 14A represents interference intensity relative to an optical length under such condition that no sample is set to the head. Due to an insertion loss of the head of the optical fiber, the SOA, or an optical connector, the light is largely attenuated. In this state, if 10 μL of 20% methanol is dropped to the head and absorbs an evanescent wave leaking from the optical fiber, interference intensity is lowered by an amount corresponding to the attenuation as indicated by a triangular mark of FIG. 14A. If the homodyne detector involves noise as indicated by the dotted line, a signal is buried in noise with the light delay optical path length of 60 m or more, making it impossible to perform high-sensitivity detection.

On the other hand, in the case of adjusting an amplification factor of SOA to correct a loss in the loop fiber, as shown in FIG. 14B, interference intensity obtained when no sample is set to the head is changed to a value indicated by the black circle from a value indicated by the triangular mark with the SOA's amplification factor of 1. Owing to the correction, even if an optical length of the delay line is increased, interference intensity is not changed. If a sample is set to the head in this state, interference intensity is as indicated by the triangular mark of FIG. 14C due to absorption to the sample. In this case, interference intensity is higher than a noise level even with the fiber length of 60 m or more unlike the triangular mark of FIG. 14B. In this embodiment, the maximum optical length of the light delay line is set to 180 m, but a light delay line of several kilometers or longer can be used for measurement. In this case, a sample having a very low absorbance can be measured.

EXAMPLE 6

Figure 15:
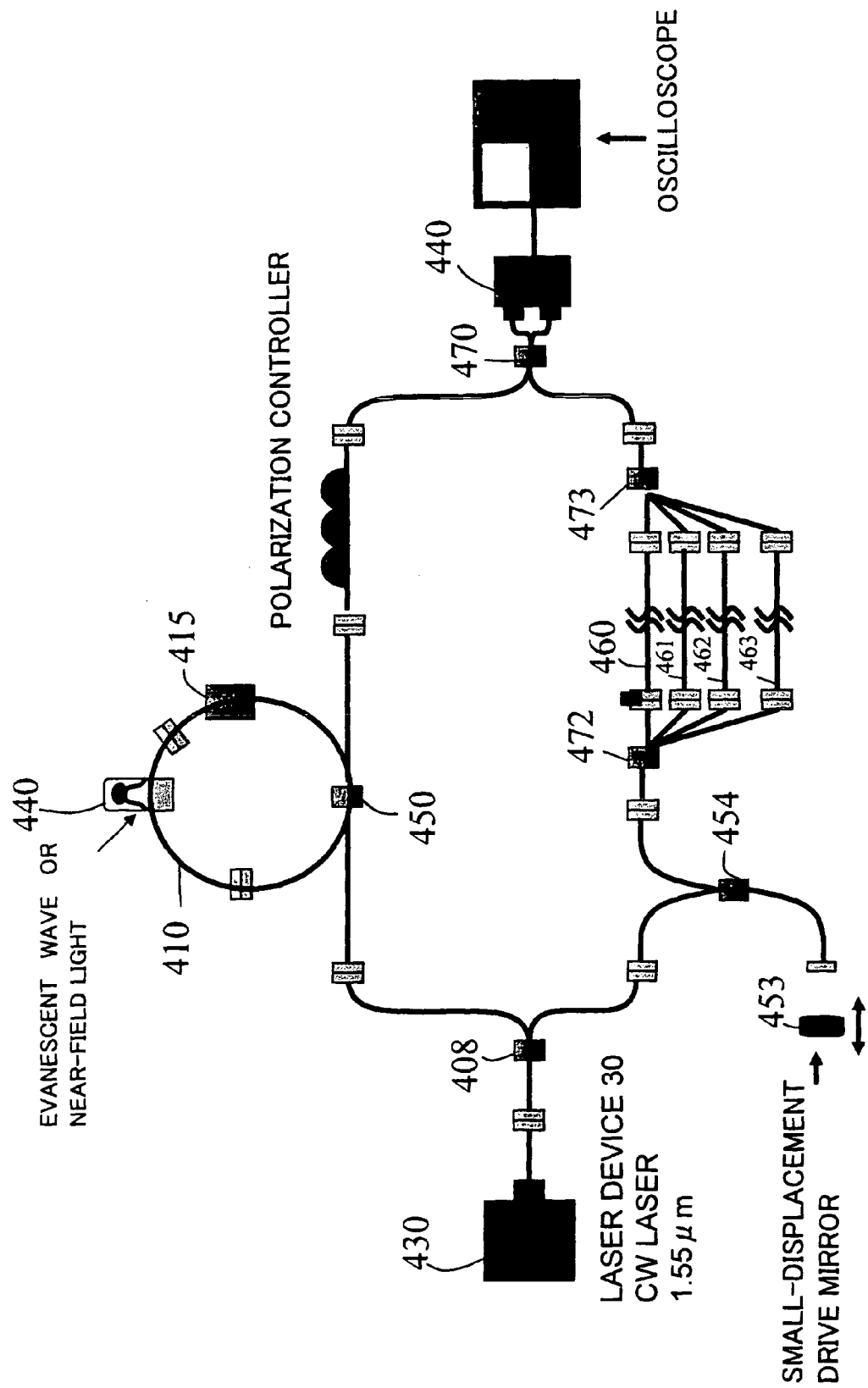
FIG. 15 is a diagram specifically showing an apparatus according to Example 6 of the present invention.
Figure 16:
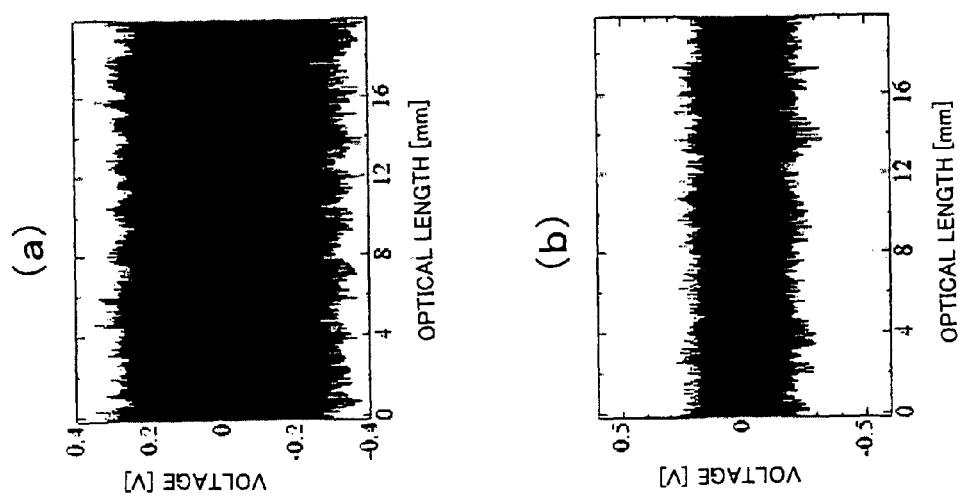
FIG. 16 is a characteristic chart showing an interference wavelength of laser obtained by the apparatus of Example 6.

FIG. 15 shows an example where a CW laser is used. The same apparatus structure as that of Example 5 as shown in FIG. 12 is used to perform similar measurement except that a CW oscillation semiconductor laser is used for the laser device. As for interference intensity obtained with varying light delay optical lengths, an intensity waveform as shown in FIG. 16(a) is measured with the homodyne detector by driving a mirror with both of the 3 m optical length and 180 m optical length. In this state, if a sample is set to a head portion and absorbs light, an interference waveform of FIG. 16(b) is obtained. Absorptance characteristics thereof can be measured with high sensitivity based on a factor of attenuation of the interference waveform. In this case, an amplification factor of an attenuated interference waveform as shown in FIG. 16(b) is increased to the interference intensity of FIG. 16(a). Then, absorptance characteristics may be determined based on the amplification factor.

EXAMPLE 7

Figure 17:
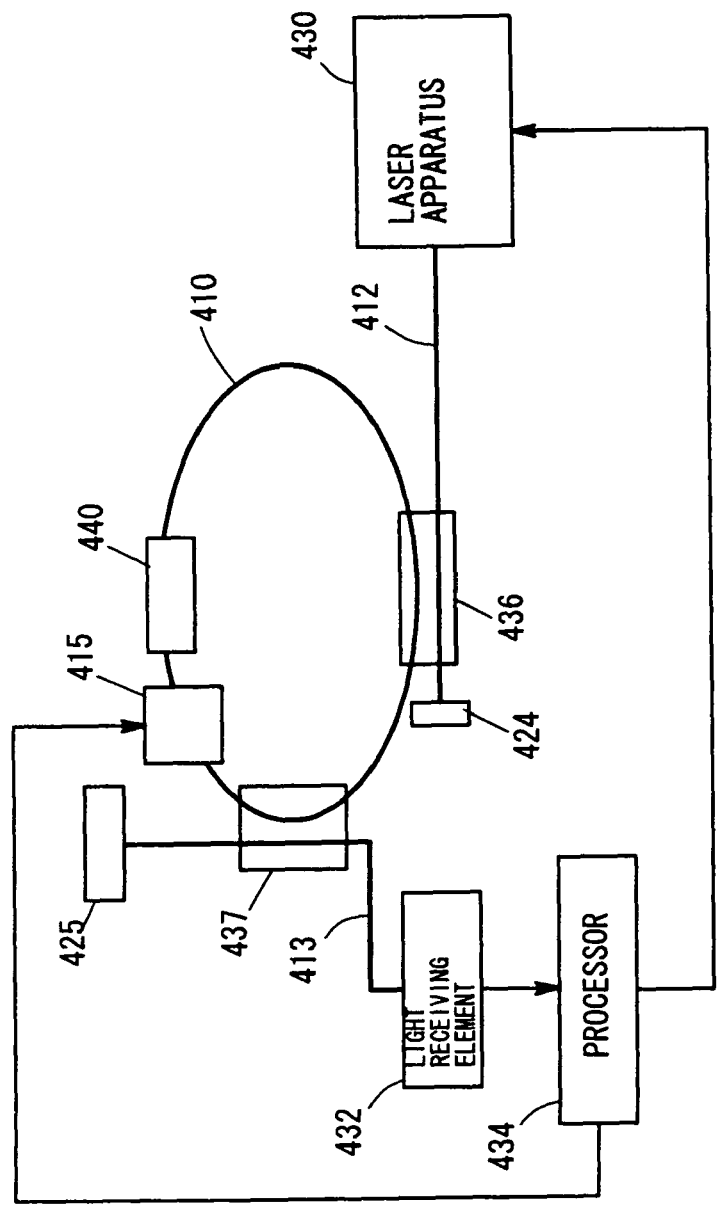
FIG. 17 is a diagram specifically showing an apparatus according to Example 7 of the present invention.

Next, Example 7 of the present invention is described. In FIG. 17, the structure regarding the light waveguide 412, the loop optical fiber 410, an insertion position of the sample 440, the detection element 432, and the processor 434 is the same as Example 4. A pulse laser is used for the laser device 430, and the first polarizer 422, the second polarizer 421, and the faraday rotator 423 are omitted.

In this example, an input system and output system of laser light to/from the optical fiber 410 are separated from each other. The input system has a terminal end 424 that allows neither light transmission nor light reflection. The terminal end is connected to the terminal end of the first light waveguide. As the additional laser light output system, a second optical directional coupling element 437 optically coupled with the optical fiber 410, and a second light waveguide 413 and a terminal end 425 coupled with the optical fiber 410 through the second optical directional coupling element 437 are provided. Then, the detection element 432 is connected to one end of the second light waveguide 413.

In this example, pulse laser light output from the laser device 430 propagates through the first light waveguide and is split to the optical fiber 410 through an optical directional coupling element 436 and circulating in the optical fiber 410. The ring down pulse light enters the detection element 432 through the second optical directional coupling element 437 and the second light waveguide 413 to circulate in the optical fiber 410. An amplification factor of an optical amplifying element 437 is subjected to feedback control of a processor 434 not to attenuate an amplitude of pulse laser light incident on the detection element 432. Then, an absorption coefficient of the sample is calculated based on the amplification factor of the amplifying element. In this case, the input system and the output system are separated, so it is unnecessary to provide the second light waveguide 413 as the output system with a polarizer or polarizing optical directional coupling element.

EXAMPLE 8

Figure 18:
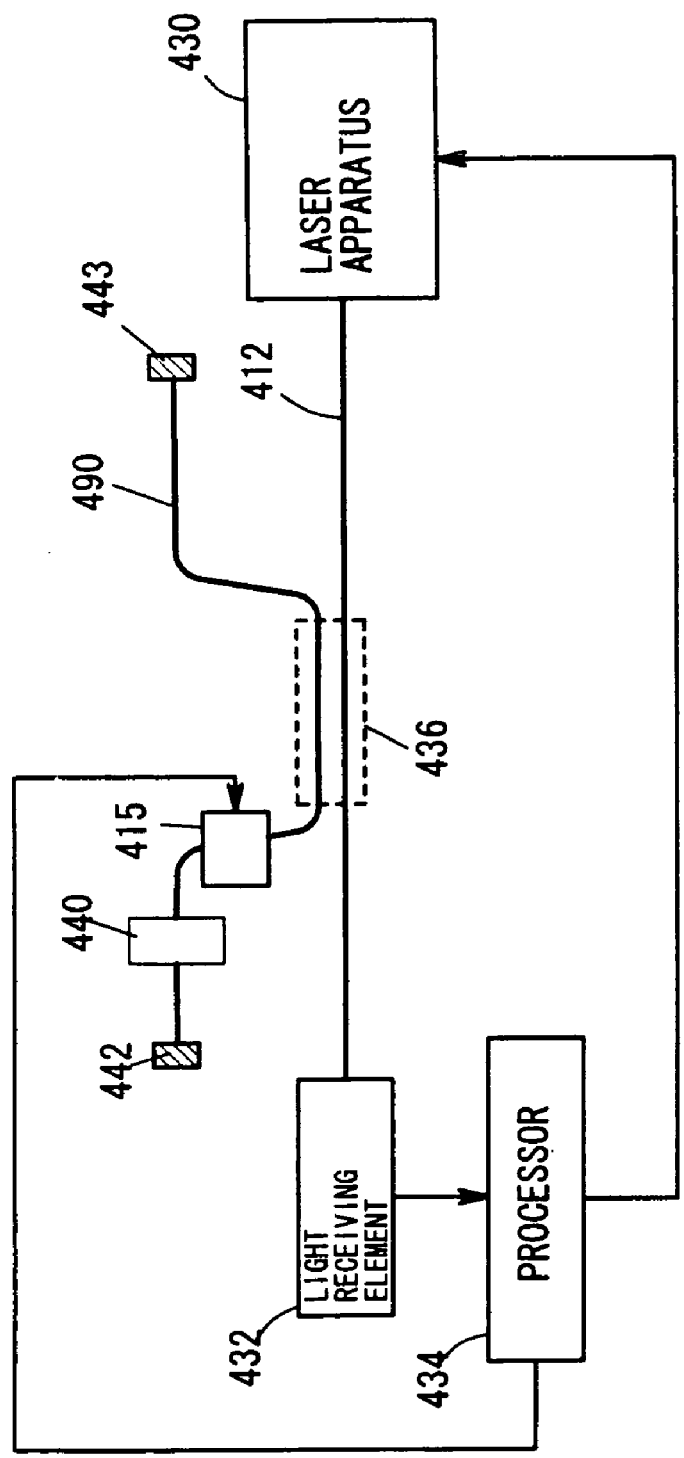
FIG. 18 is a diagram specifically showing an apparatus according to Example 8 of the present invention.

In the above example, the optical fiber 410 has a loop shape but may have a linear or curved shape as shown in FIG. 18. That is, a linear optical fiber 490 is coupled with the first light waveguide 412 by the optical directional coupling element 436. Then, both ends of the optical fiber are processed into mirror surfaces 442 and 443 to reflect light. In this case as well, pulse light reciprocating in the linear or curved optical fiber 490, not the loop one, may be output to the detection element 432 side. At this time, only ring down pulse light propagating to the sample 440 side in the optical fiber 490 can be output to the first light waveguide 412 and incident on the detection element 432 due to a function of the optical directional coupling element 436.

EXAMPLE 9

Figure 19:
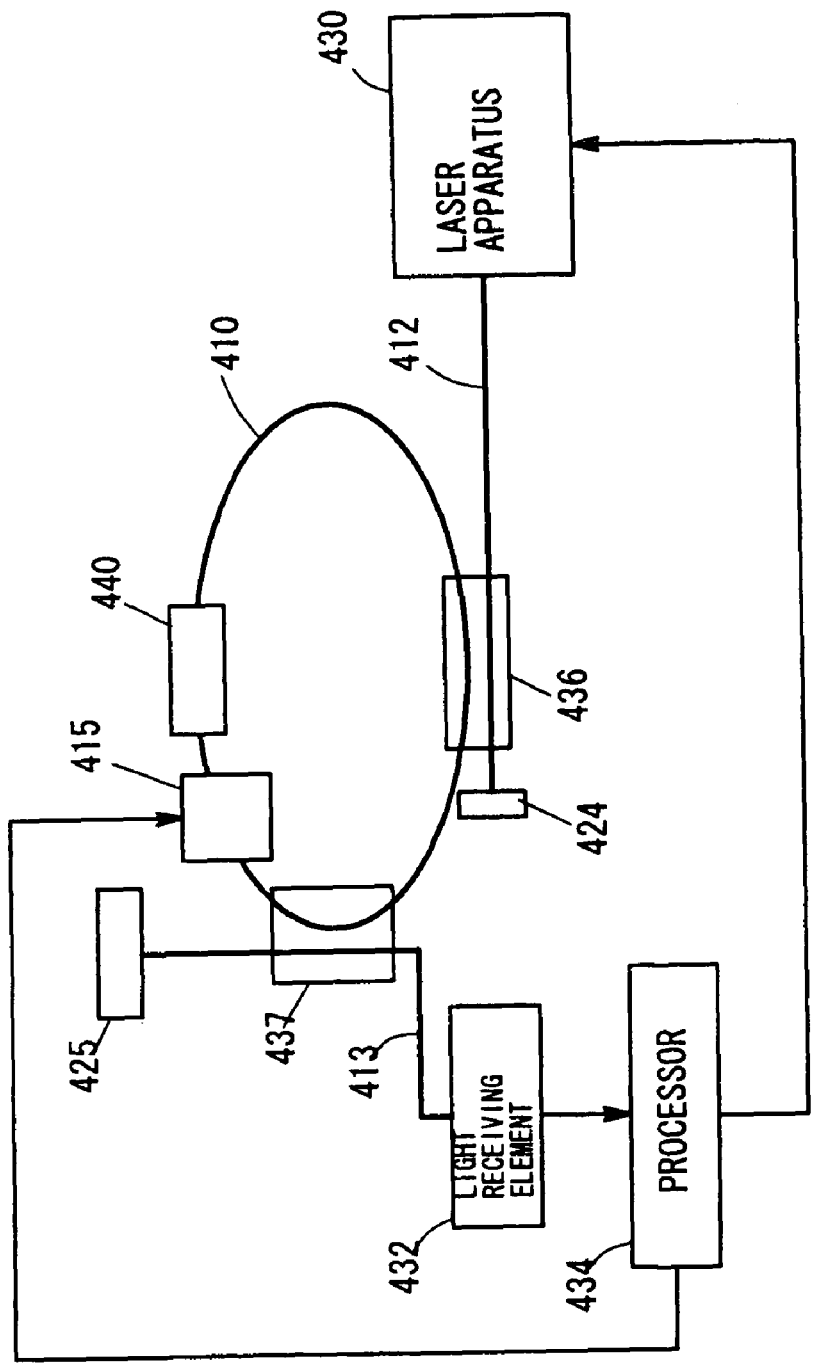
FIG. 19 is a diagram specifically showing an apparatus according to Example 9 of the present invention.

As shown in FIG. 19, a feature of this example is that the first polarizer 422, the second polarizer 421, and the faraday rotator 423 as a polarization control element are omitted, and a piezoelectric drive coupling-factor-variable coupler 436 as an optical coupling control element is provided in place of the optical directional coupling element 436 in the structure of Example 7. The other structure is the same as that of Example 7. The piezoelectric drive coupling-factor-variable coupler 436 is an element for controlling a coupling factor based on an electro-optical effect. By applying a voltage thereto, a coupling factor can be controller. A pulse voltage is applied to the piezoelectric drive coupling-factor-variable coupler 436 to enhance a coupling factor to thereby input pulse light to the optical fiber 410. The same process as Example 7 is performed to detect ring down characteristics of the pulse light with a light receiving element 432.

Further, an optical switch may be used in place of the piezoelectric drive coupling-factor-variable coupler as the optical coupling control element. That is, if the control element is an optical switch capable of connecting/disconnecting the first light waveguide 412 to/from the optical fiber 410 at high speeds, pulse light or step-down light can be incident on the optical fiber 410.

EXAMPLE 10

The above examples can be modified as follows. Under such condition that a sample 440 is not set, an amplification factor of an optical amplifying element is subjected to feedback control to prevent attenuation of the ring down light. Next, the sample 440 is set, and attenuation characteristics of the ring down light are measured to determine an attenuation constant based on the characteristics. In this case, the measurement system involves no attenuation, so an absorption coefficient of the sample alone can be measured with accuracy.

EXAMPLE 11

In Examples 4 to 0, step-down light may propagate through the optical fibers 410 and 490 in place of pulse light. In this case, in Example 4, a continuous magnetic field is applied to the faraday rotator 423 in response to continuous control signal output from the processor 434. As a result, S-polarized continuous laser light output from the second polarizer 421 is converted to P-polarized light by the faraday rotator 423. The P-polarized laser light enters the optical fibers 410 and 490 through the optical directional coupling element 436. Next, the continuous control signal is cut to stop application of the magnetic field to the faraday rotator 423. Then, S-polarized continuous laser light is output from the faraday rotator 423. This light is not incident on the optical fibers 410 and 490. Thus, in the optical fibers 410 and 490, an amplitude of the P-polarized laser light is reduced stepwise. The ring down light of the step-down light is detected. Then, an amplification factor of the amplifying element 415 is subjected to feedback control not to attenuate the light. A light absorptance of the sample can be measured based on the amplification factor.

Further, in Examples 7 and 8, a shutter may be provided to the first light waveguide 412 to suddenly stop propagation of laser light with a continuous laser used as the laser device 430. Further, it is possible to immediately stop laser oscillation. The stepped-down laser light can also propagate to the optical fibers 10 and 100. In Example 9, a coupling factor of the first light waveguide 412 and the optical fiber 410 is increased by the piezoelectric drive coupling-factor-variable coupler 436 to apply continuous laser light to the optical fibers 410 and 490. Next, the piezoelectric drive coupling-factor-variable coupler 436 is controlled to reduce a coupling factor of the first light waveguide 412 and the optical fiber 410 stepwise. Then, the incidence of the continuous laser light to the optical fibers 410 and 490 is interrupted stepwise. The ring down light of the stepped-down light is detected, and an amplification factor of the amplifying element 415 is subjected to feedback control not to attenuate the light. The absorptance of the sample can be measured based on the amplification factor.

Further, in Examples 4 to 10, an optical switch may be used in place of the optical directional coupling element 436. That is, it is possible to use an optical switch capable of switching a mode for coupling the first light waveguide 412 with the optical fibers 410 and 490, a mode for closing the optical fibers 410 and 490, and a mode for guiding light propagating in the optical fibers 410 and 490 on a downstream side of the first light waveguide 412. Besides, it is possible to use an optical switching element for switching a switch terminal in sync with a period of ring down pulse light.

Further, an amplification factor is fixed at an amplification factor of the amplifying element 415 obtained when the sample 440 is not set. Then, absorptance of the sample 440 can be measured based on an attenuation amount detected with the detection element 432 if the sample 440 is set.

Further, in Example 7 as shown in FIG. 17, continuous laser light may be introduced to the optical fiber 410. IN the case of using the continuous laser light, an amplification factor of the amplifying element 415 is small if the sample 440 is not set. If the sample 440 is set, an amplification factor of the amplifying element 415 is large due to light absorptance of the sample. The absorptance characteristics of the sample 40 can be measured based on a difference in amplification factor.

As described above, in the case of performing feedback control to prevent attenuation of an amplitude of laser light passing through the sample, a light absorptance coefficient of the sample can be measured at a predetermined laser light intensity. In addition, measurement accuracy can be improved. The laser light is amplified up to a level at which a loss of laser light in the optical fiber or optical system is negligible, so an S/N ratio can be increased to measure a loss of the sample alone with accuracy.

Fourth Embodiment

The present invention is described by way of examples but is not limited to the following examples.

EXAMPLE 12

Figure 20:
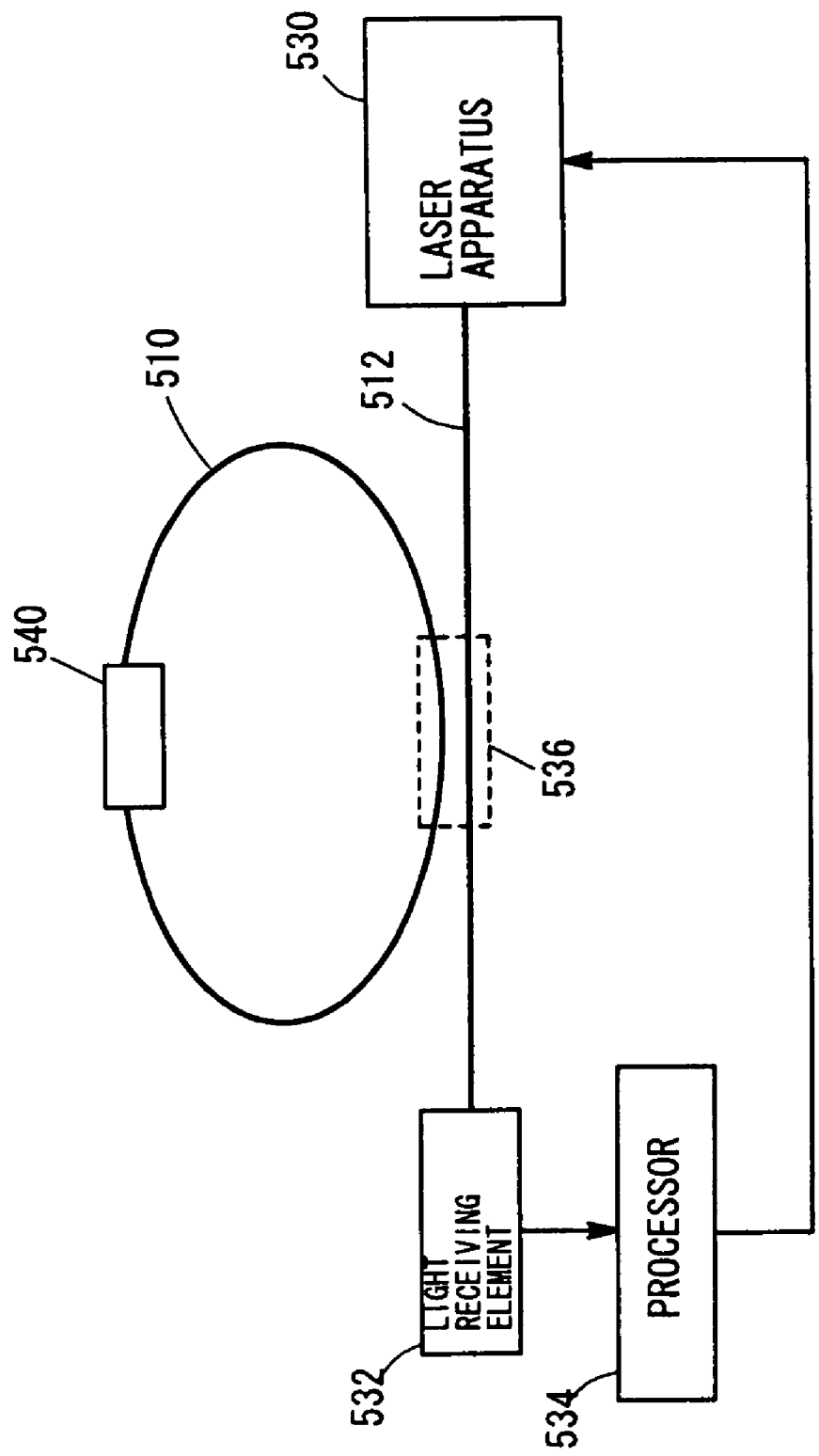
FIG. 20 is a diagram specifically showing an apparatus according to Example 12 of the present invention.

As shown in FIG. 20, a first light waveguide 512 for guiding light is optically coupled with a loop optical fiber 510 by way of an optical directional coupling element 536. A sample 540 is inserted to the light waveguide of the loop optical fiber 510. The optical fiber 510 is cut and its end faces are set face to face. The sample 540 is inserted to a space between the end faces. The apparatus is designed such that light passes through the sample 540. The first light waveguide 512 is made up of an optical fiber, which has one end connected to a broadband supercontinuum light laser device 530 and the other end connected to a light receiving element 532 and a processor 534 that calculates an attenuation coefficient based on ring down pulse light received with the light receiving element 532. A processor specified in the scope of claims is composed of the light receiving element 532 and the processor 534. The broadband supercontinuum light laser device 530 outputs broadband supercontinuum laser light through nonlinear or Raman amplification. The broadband supercontinuum laser light is well know, which is reported in, for example, Norihiko Nishizawa, Toshio Goto, "Solid Physics" Vol. 39, No. 10, (2004), pp. 665-678.

Further, the first light waveguide 512 is provided with an optical directional coupling element 536 for optically coupling the loop optical fiber 510 with the first light waveguide 512. The optical directional coupling element 536 splits only light propagated through the first light waveguide 512 to the optical fiber 510 in the travelling direction alone. If pulse laser light is input to the optical fiber 510 from the first light waveguide 512, the pulse laser light circulates in the optical fiber 510. Each time the light passes through the sample 540, an amplitude is successively reduced to obtain ring down pulse light. The ring down pulse light is output to the first light waveguide 512 from the optical fiber 510 through the directional optical coupling element 536.

A ring down attenuation coefficient of the ring down pulse light is measured with the light receiving element 532 and the processor 534 to thereby measure an attenuation coefficient of the sample. Each wavelength of the laser light is measured as above to thereby obtain wavelength absorption characteristics of the sample and identify atomic and molecular structures of the sample.

Figure 21:
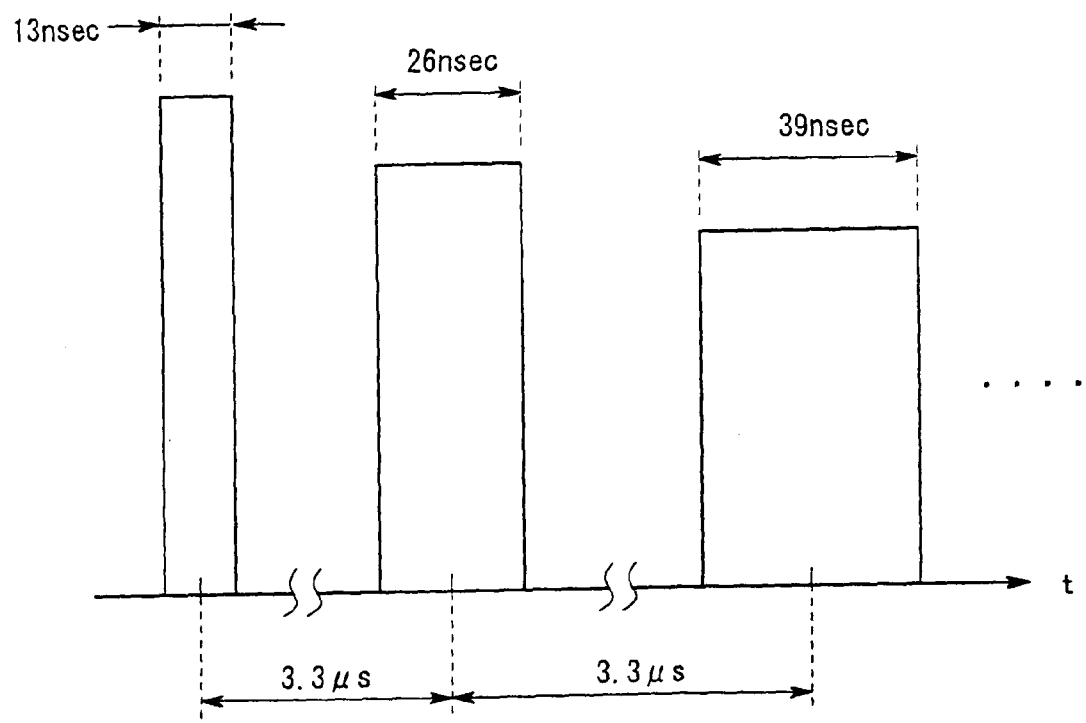
FIG. 21 is a waveform diagram of a ring down pulse waveform for illustrating the apparatus of Example 12.
Figure 22:
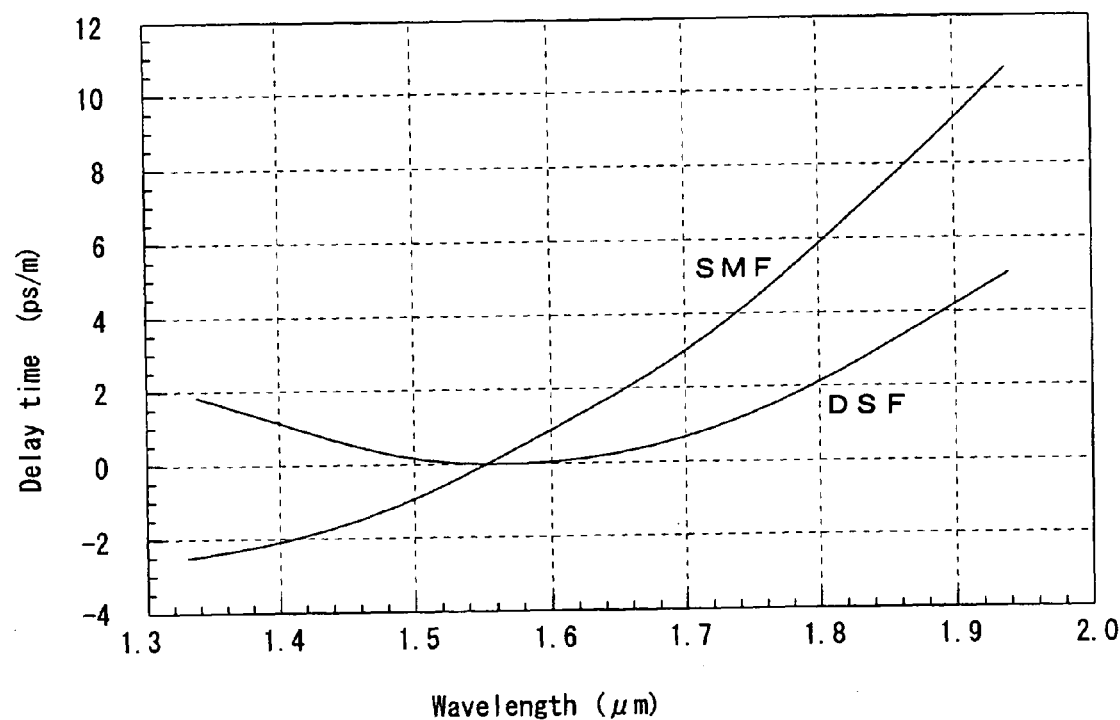
FIG. 22 is a characteristic chart showing a relationship between a wavelength and a propagation delay time of an optical fiber having strong dispersive characteristics.

In FIG. 22, SMF represents a relationship between a wavelength and a propagation delay time per one m, which is obtained if the optical fiber 510 is a single-mode high-dispersion fiber. If the wavelength is changed from 1.33 μm to 1.94 μm, a propagation delay time is changed by 13 ps/m. Hence, provided that the optical fiber 510 has a length of 1 km, if the wavelength is changed from 1.33 μm to 1.94 μm, a delay time is changed by 13 ns. That is, in the case of using broadband supercontinuum femtosecond light (100 fs ($1\times10^{-13}$ sec)) having a wavelength of 1.33 μm to 1.94 μm, the first ring down pulse has a width of 13 ns, the second ring down pulse has a width of 26 ns, and the third ring down pulse has a width of 39 ns. These ring down pulses are as illustrated in FIG. 21.

Provided that a pulse interval of the femtosecond laser light is 3 kHz, 100 ring down pulses can appear in one period. If 100 ring down pulses are generated, a pulse width is 1.3 μs, and an interval between adjacent ring down pulses is 3.3 μs, so these pulses do not overlap each other. The ring down pulses received with the light receiving element 32 as shown in FIG. 21 are sampled with a small interval, and resultant values are temporarily stored. If ring down pulses of one pulse laser light of FIG. 21 cannot be sampled at a time, pulse laser light repeatedly appears at an interval of 3 kHz, so the repetition frequency waveform is sampled to obtain a ring down pulse waveform in one period.

If ring down pulses of one pulse laser light are obtained as shown in FIG. 21, a relationship between the time and the wavelength of FIG. 21 is constant, so the wavelength can be derived from the time. For example, assuming that the characteristic chart of FIG. 22 is a linear one, and $y=k(x-x_0)+y_0$ where x represents a wavelength, $x_0$ represents a central wavelength of 1.64 μm, y represents a delay time, and $y_0$ represents a delay time at the wavelength $x_0$. For ease of explanation, $y_0=0$. In the waveform of FIG. 21, if $y_0=0$, and the maximum wavelength change from $x_0$ is Δx(0.3 μm), a delay time per Δx is 6.5 ns. Hence, k=6.5 ns/Δx=21.67 ns/μm and $y_1=k(x-x_0)$ for the one-time ring down pulse. For the two-time ring down pulse, $y_2=2k(x-x_0)$. For the three-time ring down pulse, $y_3=3k(x-x_0)$. Here, y represents a delay time from the center of each ring down pulse, i.e., a reference time of each ring down pulse corresponding to the central wavelength $x_0$.

If the ring down pulse waveform of FIG. 21 is obtained, a wavelength x corresponding to a time sequence $y_1, y_2, \ldots, y_n$ can be calculated based on the above relationship. An attenuation coefficient α of the ring down pulse is calculated based on attenuation characteristics of the pulse in the time sequence $y_1, y_2, \ldots, y_n$ with respect to the wavelength x. The coefficient is calculated for each wavelength x to thereby obtain an attenuation coefficient α(x) of the wavelength can be determined. In practice, the wavelength propagating delay time characteristic of FIG. 22 is not linear, so a relationship between the time and wavelength is determined based on the curve.

As described above, if the optical fiber 10 has a length of 1 km, a pulse width of the ring down pulse is 13 ns or more, and that of the 10-time ring down pulse is 130 ns. Therefore, a wide pulse width can be secured to facilitate sampling of a waveform and increase a wavelength resolution. Further, even if the optical fiber 10 has a length of 100 m, a pulse width of the ring down pulse is 1.3 ns or more, and that of the 10-time ring down pulse is 13 ns. Therefore, the waveform of FIG. 21 can be sampled.

A repetition frequency of the pulse laser light is related to the length of the optical fiber 10. If the total length is 1 km, the ring down pulses are output at intervals of 3.3 μs. If a repetition frequency of pulse laser light is 1 kHz (period of 1×10$^{-3}$ sec), 300 ring down pulses can appear in one pulse period. On the other hand, if the total length is 100 m, the ring down pulses are output at intervals of 0.33 μs. If 100 ring down pulses are necessary to be generated in one pulse period, the pulse frequency should be set to 30 kHz.

Since the ring down pulse includes the attenuation according to measurement system itself, in practice, ring down characteristics of pulse laser light are measured as reference characteristics under such condition that no sample is set. Then, attenuation characteristics as deviation of the ring down characteristics from reference characteristics are obtained under such condition that a sample is measured. An adsorption coefficient of the sample is measured based on the attenuation characteristics. The absorptance coefficient can be determined based on the attenuation coefficient of the exponent function with the horizontal axis representing the number of ring down processes and the vertical axis representing an amplitude of the ring down pulse light. Further, the wavelength absorption characteristics can be similarly obtained by measuring an attenuation coefficient of the ring down characteristics with varying wavelengths of laser light. At the time of determining the characteristics, even though an absolute value of the absorptance coefficient is uncertain, if relative adsorption characteristics are obtained as wavelength characteristics, a sample can be identified.

Further, in Example 12, the optical directional coupling element 536 is well known. The optical directional coupling element can guide the ring down pulse light of laser light to the detection element 532. Further, if its coupling factor is changed, intensity of light circulating in the optical fiber 510 can be adjusted. As a result, an attenuation degree of light input to the detection element 532 can be adjusted, so an attenuation coefficient can be measured with the same dynamic range. Hence, measurement accuracy can be improved.

EXAMPLE 13

Figure 23:
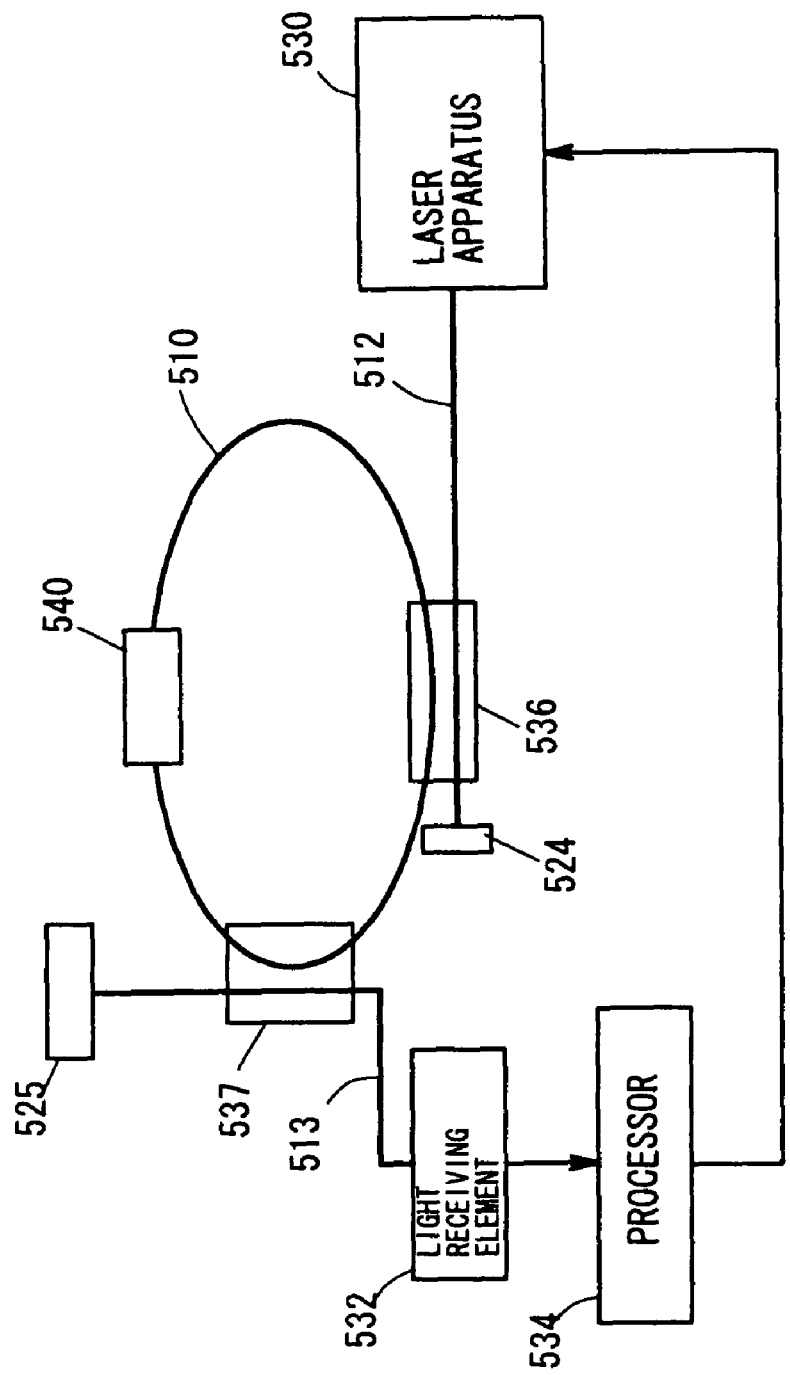
FIG. 23 is a diagram specifically showing an apparatus according to Example 13 of the present invention.

Next, Example 13 of the present invention is described. In FIG. 23, the structure regarding the light waveguide 512, the loop optical fiber 510, an insertion position of the sample 540, the detection element 532, and the processor 534 is the same as Example 12.

In Example 13, an input system and output system of laser light to/from the optical fiber 510 are separated from each other. The input system is almost similar to that of Example 12 except that the first light waveguide 512 has a terminal end 524 that allows neither light transmission nor light reflection. As the additional laser light output system, a second optical directional coupling element 537 optically coupled with the optical fiber 510, and a second light waveguide 513 and a terminal end 525 coupled with the optical fiber 510 through the second optical directional coupling element 537 are provided. Then, the detection element 532 is connected to one end of the second light waveguide 513.

In this example, pulse laser light is guided to the optical fiber 510 similar to Example 12. The ring down pulse light enters the light receiving element 532 through the second optical directional coupling element 537 and the second optical directional coupling element 513 to circulate in the optical fiber 510. In this case, the input system and the output system are separated, so it is unnecessary to provide the second light waveguide 513 as the output system with a polarizer or polarizing optical directional coupling element.

EXAMPLE 14

Figure 24:
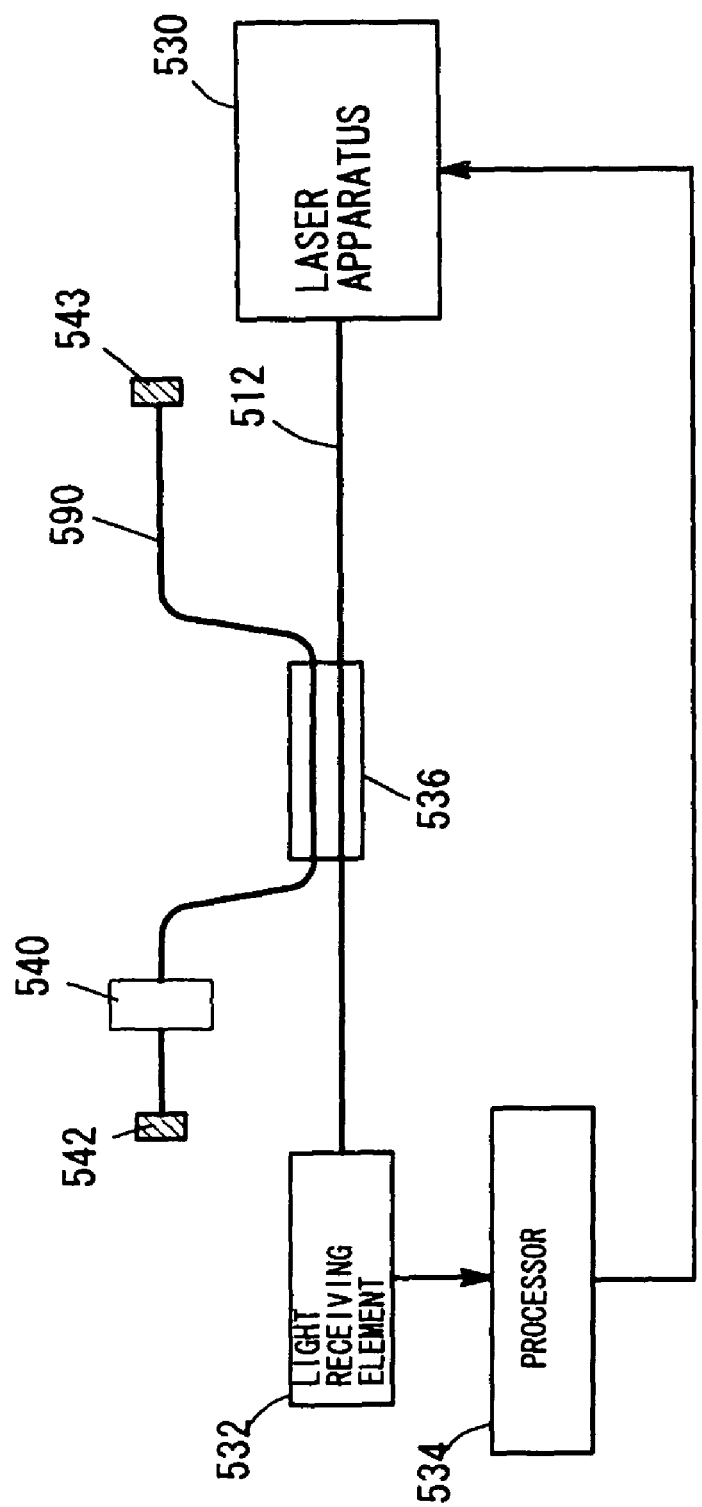
FIG. 24 is a diagram specifically showing an apparatus according to Example 14 of the present invention.

In Example 13, the optical fiber 410 has a loop shape but may have a linear or curved shape as shown in FIG. 24. That is, a linear optical fiber 590 is coupled with the first light waveguide 512 by the optical directional coupling element 536. Then, both ends of the optical fiber are processed into mirror surfaces 542 and 543 to reflect light. In this case as well, pulse light reciprocating in the linear or curved optical fiber 590, not the loop one, may be output to the detection element 532 side. At this time, only ring down pulse light propagating to the sample 540 side in the optical fiber 590 can be output to the first light waveguide 512 and incident on the detection element 532 due to a function of the optical directional coupling element 536.

Industrial Applicability

The present invention is applicable to analysis of a ultrathin sample or a very small amount of sample, such as identification of the sample, and to analysis of a small amount of substance or DNA, which is treated with plasma.

Further, the present invention is effective for spectroscopy of a liquid, a gas, DNA, protein, and other such biological materials, an organic material, an inorganic material, and thin film. Further, according to the invention, it is possible to obtain waveform absorptance characteristics based on ring down pulse waveform without changing a wavelength of a laser light source.

The invention claimed is:

1. A spectroscopy method, comprising:
    guiding pulse laser light to an optical fiber, which mutually reacts with a sample to be measured of a light absorptance characteristic;
    outputting ring down pulse light obtained through light absorption of the sample;
    measuring an absorptance characteristic of the sample based on an attenuation characteristic of the ring down pulse light; and
    setting the pulse laser light as wide-spectrum laser light, setting the optical fiber as a dispersive optical fiber, and increasing a pulse width of the ring down pulse light to measure a wavelength absorptance characteristic based on a ring down attenuation constant of a pulse train with respect to a time sequence corresponding to a wavelength.

2. A spectroscope for measuring a light absorption characteristic of a sample, comprising:
    an optical fiber for guiding laser pulse light to the sample to be measured of a light absorption characteristic;
    a laser device for generating wide-spectrum laser pulse light; and
    a processor for increasing a pulse width of ring down pulse light circulating or reciprocating in the optical fiber, outputting the ring down pulse light to the outside, and measuring a wavelength absorptance characteristic based on a ring down attenuation constant of a pulse train with respect to a time sequence corresponding to a wavelength in accordance with an attenuation characteristic of the ring down pulse light.

3. The spectroscope according to claim 2, further comprising:
    a first light waveguide optically coupled with the optical fiber; and
    an optical directional coupling element for optically coupling the first light waveguide with the optical fiber; the first light waveguide having one end connected to the laser device and the other end connected to a light receiving element of the processor, which receives the ring down pulse light.

4. The spectroscope according to claim 2, wherein another optical coupling element provided separately from the optical directional coupling element in the optical fiber is used to output the ring down pulse light to a second light waveguide different from the first light waveguide, and the second light waveguide is connected to the light receiving element of the processor.

* * * * *